US012661312B2

(12) United States Patent
Sabelle et al.

(10) Patent No.: US 12,661,312 B2
(45) Date of Patent: Jun. 23, 2026

(54) PROCESS FOR DYEING KERATIN MATERIALS USING A DIRECT DYE AND AN UNSATURATED HETEROCYCLIC SALT, AND COMPOSITION COMPRISING SAME

(71) Applicant: L'OREAL, Paris (FR)

(72) Inventors: Stéphane Sabelle, Aulnay-sous-Bois (FR); Olivier Guerard, Aulnay-sous-Bois (FR)

(73) Assignee: L'Oreal, Paris (FR)

(*) Notice: Subject to any disclaimer, the term of this patent is extended or adjusted under 35 U.S.C. 154(b) by 1073 days.

(21) Appl. No.: 17/415,666

(22) PCT Filed: Dec. 17, 2019

(86) PCT No.: PCT/EP2019/085636

§ 371 (c)(1),
(2) Date: Jun. 17, 2021

(87) PCT Pub. No.: WO2020/127255

PCT Pub. Date: Jun. 25, 2020

(65) Prior Publication Data

US 2022/0040075 A1 Feb. 10, 2022

(30) Foreign Application Priority Data

Dec. 21, 2018 (FR) ...................................... 1874060

(51) Int. Cl.

| | |
|---|---|
| ***A61K 8/49*** | (2006.01) |
| ***A61K 8/35*** | (2006.01) |
| ***A61K 8/41*** | (2006.01) |
| ***A61Q 5/06*** | (2006.01) |
| ***A61Q 5/10*** | (2006.01) |

(52) U.S. Cl.

CPC .......... *A61K 8/4926* (2013.01); *A61K 8/4946* (2013.01); *A61K 8/4953* (2013.01); *A61K 8/496* (2013.01); *A61Q 5/065* (2013.01); *A61K 2800/4322* (2013.01); *A61K 2800/882* (2013.01)

(58) Field of Classification Search

None

See application file for complete search history.

(56) References Cited

U.S. PATENT DOCUMENTS

| | | | | |
|---|---|---|---|---|
| 3,100,739 | A | | 8/1963 | Kaiser et al. |
| 3,524,842 | A | | 8/1970 | Grossmann et al. |
| 3,578,386 | A | | 5/1971 | Kalopissis et al. |
| 3,617,163 | A | | 11/1971 | Kalopissis et al. |
| 3,817,698 | A | | 6/1974 | Kalopissis et al. |
| 3,869,454 | A | | 3/1975 | Lang et al. |
| 3,955,918 | A | | 5/1976 | Lang |
| 4,025,301 | A | | 5/1977 | Lang |
| 4,519,947 | A | | 5/1985 | Hattori et al. |
| 4,886,517 | A | | 12/1989 | Bugaut et al. |
| 5,637,115 | A | * | 6/1997 | Balzer .................. A61K 8/4926 8/408 |
| 5,708,151 | A | | 1/1998 | Möckli |
| 5,879,413 | A | | 3/1999 | Pengilly et al. |
| 5,888,252 | A | | 3/1999 | Möckli |
| 5,919,273 | A | | 7/1999 | Rondeau et al. |
| 5,944,360 | A | | 8/1999 | Crapart |
| 5,993,490 | A | | 11/1999 | Rondeau et al. |
| 6,045,591 | A | | 4/2000 | Deneulenaere |
| 6,136,042 | A | | 10/2000 | Maubru |
| 6,179,881 | B1 | | 1/2001 | Henrion et al. |
| 6,451,069 | B2 | | 9/2002 | Matsunaga et al. |
| 6,458,167 | B1 | | 10/2002 | Genet et al. |
| 6,652,601 | B2 | | 11/2003 | Sauter et al. |
| 6,790,239 | B1 | | 9/2004 | Moeller et al. |
| 6,797,013 | B1 | | 9/2004 | Lang et al. |
| 6,863,883 | B1 | | 3/2005 | Tsujino et al. |
| 6,997,963 | B2 | | 2/2006 | Guerin |
| 8,025,701 | B2 | | 9/2011 | De Boni |
| 8,071,080 | B2 | | 12/2011 | Giroud |
| 9,498,927 | B2 | | 11/2016 | Watkins et al. |
| 9,839,591 | B2 | | 12/2017 | David |
| 2004/0005286 | A1 | * | 1/2004 | Giroud ..................... A61Q 5/02 424/70.28 |
| 2006/0021160 | A1 | | 2/2006 | Lagrange et al. |
| 2007/0251028 | A1 | | 11/2007 | Samain et al. |
| 2013/0227797 | A1 | | 9/2013 | Greaves |
| 2014/0215728 | A1 | | 8/2014 | Charrier et al. |
| 2015/0101132 | A1 | | 4/2015 | David et al. |

(Continued)

FOREIGN PATENT DOCUMENTS

| | | | |
|---|---|---|---|
| DE | 2527638 | A1 | 5/1976 |
| DE | 2538363 | A1 | 5/1976 |
| DE | 4137005 | A1 | 5/1993 |
| DE | 4220388 | A1 | 12/1993 |
| DE | 10 2005 032798 | A1 | 1/2007 |
| DE | 10 2006 017901 | A1 | 10/2007 |
| EP | 0714954 | A2 | 6/1996 |
| EP | 0850636 | A1 | 7/1998 |
| EP | 0850637 | A1 | 7/1998 |
| EP | 0860636 | A1 | 8/1998 |
| EP | 0918053 | A1 | 5/1999 |
| EP | 0920856 | A1 | 6/1999 |
| EP | 1062940 | A1 | 12/2000 |
| EP | 1133975 | A2 | 9/2001 |

(Continued)

OTHER PUBLICATIONS

WO2007006418—Google English translation (in part—pp. 1-5, 92-93 and 100-102). (Year: 2007).*

(Continued)

*Primary Examiner* — Kyung S Chang

(74) *Attorney, Agent, or Firm* — The Marbury Law Group, PLLC

(57) ABSTRACT

The present invention relates to a cosmetic process for treating keratin materials, in particular keratin fibers, preferably human keratin fibers such as the hair, using a) one or more direct dyes and b) one or more particular heterocyclic salts, to a composition comprising ingredients a) and b) and to a kit comprising a) and b).

20 Claims, No Drawings

(56) References Cited

U.S. PATENT DOCUMENTS

| | | | |
|---|---|---|---|
| 2015/0113742 | A1 | 4/2015 | David |
| 2015/0224041 | A1 | 8/2015 | Greaves |

FOREIGN PATENT DOCUMENTS

| | | | |
|---|---|---|---|
| EP | 1133976 | A2 | 9/2001 |
| EP | 1199065 | A2 | 4/2002 |
| EP | 1362572 | A1 | 11/2003 |
| EP | 2359804 | A2 | 8/2011 |
| FR | 1221122 | A | 5/1960 |
| FR | 1516943 | A | 2/1968 |
| FR | 1540423 | A | 9/1968 |
| FR | 1560664 | A | 3/1969 |
| FR | 1567219 | A | 5/1969 |
| FR | 2189006 | A1 | 1/1974 |
| FR | 2275462 | A1 | 1/1976 |
| FR | 2285851 | A1 | 4/1976 |
| FR | 2570946 | A1 | 4/1986 |
| FR | 2757385 | A1 | 6/1998 |
| FR | 2788433 | A1 | 7/2000 |
| FR | 2983073 | A1 | 5/2013 |
| GB | 738585 | A | 10/1955 |
| GB | 1163385 | A | 9/1969 |
| GB | 1195386 | A | 6/1970 |
| GB | 1514466 | A | 6/1978 |
| JP | H6-49775 | U | 7/1994 |
| JP | 2003-513898 | A | 4/2003 |
| JP | 2003-523375 | A | 8/2003 |
| JP | 2003-335640 | A | 11/2003 |
| JP | 2004-036072 | A | 2/2004 |
| JP | 2009-203211 | A | 9/2009 |
| JP | 2010-506892 | A | 3/2010 |
| JP | 2015-517558 | A | 6/2015 |
| JP | 2016-512850 | A | 5/2016 |
| WO | 95/01772 | A1 | 1/1995 |
| WO | 97/44004 | A1 | 11/1997 |
| WO | 99/48465 | A1 | 9/1999 |
| WO | 01/66646 | A1 | 9/2001 |
| WO | 03/029359 | A1 | 4/2003 |
| WO | 2007/006418 | A1 | 1/2007 |
| WO | 2007/118616 | A1 | 10/2007 |
| WO | 2013/079528 | A1 | 6/2013 |
| WO | 2013/175002 | A2 | 11/2013 |
| WO | 2018/115155 | A1 | 6/2018 |
| WO | 2018/115156 | A1 | 6/2018 |
| WO | 2020/127250 | A1 | 6/2020 |

OTHER PUBLICATIONS

Anonymous: Eosin B, Datasheet Product Overview, Mar. 3, 2020, XP055673858, retrieved from the internet: URL: https://www.hellobio.com/hellobiocatalog/download/productpdf/?id=770 [retrieved on Mar. 4, 2020].

Non-Final Office Action for copending U.S. Appl. No. 17/415,665, dated May 6, 2022.

STIC Search Report dated Apr. 20, 2022.

International Search Report and Written Opinion for counterpart Application No. PCT/EP2019/085630, dated Mar. 17, 2020.

International Search Report and Written Opinion for counterpart Application No. PCT/EP2019/085636, dated Mar. 24, 2020.

Zviak, Charles, "Science Des Traitements Capillaires," [Hair Treatment Science], published by Masson, 1988, pp. 214-279.

Alberti, G. et al., "Ricerche Sui Coloranti Cationici Per Fibra Acrilica," La Chimica E L'Industria, (Milan), (Sep. 1974), vol. 56, No. 9, pp. 600-602 (English translation unavailable).

Alberti, Guido et al., "Cationic Dyes for Acrylic Fibres. V. Catonic Dyes Derived from Several Heterocyclic Amines with Two or More Heteroatoms," Annali di Chimica, (Rome), (1975), 65(5-6), pp. 305-314.

Albert, Guido et al., "Thermodynamic Features in Acrylic Fiber Dyeing with Basic Dyes," Textile Research Journal, (Feb. 1984), 54(2), pp. 105-107.

Balaban, Alexandru et al., "Reactions of Pyrylium Salts with Nucleophiles," Revue Roumaine de Chimie, (1998), 33(4), pp. 377-383.

Prostakov, N.S. et al., "2,5-Dimethyl-4-Nitroaryl (Aminoaryl) Pyridines in Synthesis," Chemistry and Chemical Technology, published by Ivanovo Chemical Technological Institute, vol. 22, No. 5, pp. 548-553 (No translation available).

Yen, Feng-Wen et al., "The Design and Synthesis of Bisazo Series Compound Used in Organophotoconductor," MRL Bull. Res. Dev., vol. 6, No. 2 (1992), pp. 21-27.

Neidlein, Richard et al., "Synthese von Substituierten Pyridiniumsalzen," German Monatshefte für Chemie, (1975), vol. 106, No. 3, pp. 643-648 (English translation unavailable).

Savarino et al., "Disperse and Cationic Dyes from Aminophenyl-X-Azolo-Pyridines," Dyes and Pigments, vol. 11, (1989), pp. 163-172.

Seidler, Von Eberhard et al., "Die Eignung Verschiedener Ditetrazoliumsalze als Reduktionsindikatoren in der Enzymhistochemie," Acta histochem. Bd. 61 (1), 1978, pp. 48-52. (The qualification of different diterazolium salts as indicators in the oxido-reductase histochemistry).

Stashkevich, V.V. et al., "Bisformazans and Bistetrazolium Salts, Derivatives of Quinaldine Quaternary Salts," Zhurnal Obshchei Khimii, (1970), 40(1), pp. 195-202.

Tien, Hsien-Ju et al., "Syntheses of New Azo Dyestuff Containing a Sydnone Ring," Journal of the Chinese Chemical Society, (Taipei), (1998), 45(1), pp. 209-211.

Viscardi, Guido et al., "Disperse and Cationic Azo Dyes from Heterocyclic Intermidiates," Dyes and Pigments, vol. 19, No. 1, (1992), pp. 69-79.

Zhousheng, Y., "Research and Application of the Coordination Reaction of New Fluorescent Reagent CCPAR and Cu (II)," Lihua Jianyan, Huaxue Fence, vol. 29, No. 4, 1993, pp. 233-234.

Translation of Japanese Office Action for counterpart Application No. 2021-535904, dated Jun. 20, 2022.

Translation of Japanese Office Action for counterpart Application No. 2021-535996, dated Jun. 27, 2022.

Final Office Action for copending U.S. Appl. No. 17/415,665, dated Aug. 29, 2022.

* cited by examiner

PROCESS FOR DYEING KERATIN MATERIALS USING A DIRECT DYE AND AN UNSATURATED HETEROCYCLIC SALT, AND COMPOSITION COMPRISING SAME

CROSS REFERENCE TO RELATED APPLICATION

This is a national stage application of PCT/EP2019/085636, filed internationally on Dec. 17, 2019, which claims priority to French Application No. 1874060, filed on Dec. 21, 2018, both of which are incorporated by reference herein in their entireties.

The present invention relates to a cosmetic process for treating keratin materials, in particular keratin fibers, preferably human keratin fibers such as the hair, using a) one or more direct dyes and b) one or more particular heterocyclic salts, to a composition comprising ingredients a) and b) and to a kit comprising a) and b).

It is known practice to dye keratin fibers and in particular human hair with dye compositions containing oxidation dye precursors, which are generally known as oxidation bases, such as ortho- or para-phenylenediamines, ortho- or para-aminophenols and heterocyclic compounds. These oxidation bases are generally combined with couplers. These bases and couplers are colorless or weakly colored compounds, which, when combined with oxidizing products, may give rise to colored compounds by a process of oxidative condensation.

This type of oxidation dyeing makes it possible to obtain "permanent" colorings.

Moreover, it is known practice to dye keratin fibers and in particular human hair with dye compositions containing direct dyes. The standard dyes that are used are, in particular, dyes of the nitrobenzene, anthraquinone, nitropyridine, azo, xanthene, acridine, azine or triarylmethane type, or natural dyes. These dyes are colored or coloring molecules that have affinity for keratin fibers.

Compositions containing one or more direct dyes are applied to the keratin fibers for a time necessary to obtain the desired coloring, and are then rinsed out. The resulting colorings are particularly chromatic colorings, but are, however, temporary or semi-permanent since the nature of the interactions that bind the direct dyes to the keratin fiber and their desorption from the surface and/or the core of the fiber are responsible for their weak dyeing power and their poor persistence with respect to washing or perspiration.

Direct dyeing products notably make it possible to modify the natural color of the hair, or to cover white hairs. However, the intensity of the coloring obtained by using these products is occasionally judged as being too weak relative to the expectations of users on the day of application.

Moreover, the use of certain dyes, notably of anionic type, has a tendency to stain the scalp during the dyeing of the hair.

In addition, direct colorings have the drawback of fading out over time, in particular under the action of UV, inclement weather and successive shampooing.

The Applicant has now discovered, surprisingly, that a cosmetic process for treating keratin materials, in particular keratin fibers, notably human keratin fibers such as the hair, comprising the application to said keratin fibers of one or more direct dyes and one or more unsaturated heterocyclic salts, makes it possible notably to obtain better color build-up, and, furthermore, the colors are vivid and chromatic.

Thus, the invention relates to a process for dyeing keratin materials, in particular keratin fibers, preferably human keratin fibers such as the hair, using:

a) at least one direct dye, which is preferably anionic or neutral; and b) at least one unsaturated heterocyclic salt of formula (A) and also the optical, geometrical or tautomeric isomers thereof, and the solvates such as hydrates:

(A)

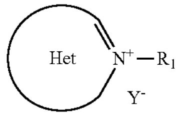

in which formula (A):

Het represents a 5- to 10-membered (preferentially 5- or 6-membered) cationic unsaturated aromatic heterocyclic group comprising, besides the ammonium, from 1 to 3 heteroatoms, preferentially 1 or 2 nitrogen or oxygen atoms, preferably 1 nitrogen atom, said heterocyclic group being optionally substituted with one or more groups $R'_1$ or $R_2$;

$R_1$ and $R'_1$, which may be identical or different, represent a linear or branched, saturated or unsaturated $(C_1-C_{12})$ hydrocarbon-based group optionally substituted notably with one or more groups chosen from hydroxyl, amino, $(C_1-C_6)$dialkylamino, $(C_1-C_6)$alkylamino, carboxyl, carboxylate, carbamide, $(C_1-C_4)$alkoxy, —$SO_3H$, sulfonate and phenyl; and $R^2$ represents a hydroxyl radical, an amino radical, a linear or branched, saturated or unsaturated $(C_1-C_{12})$ hydrocarbon-based group optionally substituted notably with one or more groups chosen from hydroxyl, amino, $(C_1-C_6)$dialkylamino, $(C_1-C_6)$alkylamino, carboxyl, carboxylate, carbamide, $(C_1-C_4)$alkoxy, —$SO_3H$, sulfonate and phenyl; and $Y^-$ represents an anionic counterion;

it being understood that:

when one of the hydrocarbon-based groups of $R_1$, $R'_1$ or $R_2$ is substituted with a carboxylate or sulfonate group, then $Y^-$ is absent to ensure the electrical neutrality of the salt of formula (A);

ingredients a) and b) are applied to said materials, together or separately, i.e. sequentially; preferably, ingredients a) and b) are applied together to said fibers.

Another subject of the invention is a cosmetic composition comprising ingredients a) and b) as defined previously. Another subject of the invention is the use of the composition for dyeing hair fibers, in particular human keratin fibers such as the hair.

Other subjects, characteristics, aspects and advantages of the invention will emerge even more clearly on reading the description and the examples that follow.

In the subsequent text, and unless otherwise indicated:

the dyes according to the invention contain one or more chromophores, and these dyes are capable of absorbing light at a wavelength labs particularly of between 400 and 700 nm inclusive;

the "fluorescent" dyes according to the invention are dyes containing at least one fluorescent chromophore, and these dyes are capable of absorbing in the visible range at a wavelength $\bullet_{abs}$ particularly inclusively between 400 and 800 nm and of re-emitting in the visible range at a longer wavelength $I_{em}$ than that absorbed, inclusively between 400 and 800 nm. The difference between the absorption and emission wavelengths, also known as the Stoke's shift, is inclusively between 1 nm and 100 nm. More preferentially, fluorescent dyes are dyes that are capable of absorbing at a wavelength $•_{abs}$ inclusively between 420 and 550 nm and of re-emitting in the visible range at a wavelength $•_{em}$ inclusively between 470 and 600 nm;

an "alkylene" group represents a linear or branched $C_1$-$C_{10}$; particularly $C_1$-$C_6$, more particularly $C_1$-$C_2$; acyclic hydrocarbon-based divalent chain optionally substituted with one or more groups, which may be identical or different, chosen from i) hydroxyl, ii) ($C_1$-$C_2$)alkoxy, iii) (poly)hydroxy($C_2$-$C_4$)alkoxy(di)($C_1$-$C_2$)(alkyl)amino, iv) $R^a$—$Z^a$—C($Z^b$)—$Z^c$—, and v) $R^a$—$Z^a$—S(O)$_t$—$Z^c$— with $Z^a$, $Z^b$, which may be identical or different, representing an oxygen or sulfur atom or a group $NR^{a'}$, $Z^c$, representing a bond, an oxygen or sulfur atom, or a group $NR^a$; $R^a$, representing an alkali metal, a hydrogen atom, an alkyl group or is absent if another part of the cationic molecule and $R^{a'}$ representing a hydrogen atom or an alkyl group and t is equal to 1 or 2; preferably, the "alkylene" group represents a group —$(CH_2)_P$— with p being an integer between 1 and 6, preferably between 1 and 4;

an "optionally substituted hydrocarbon-based" group represents a hydrocarbon-based chain, particularly of $C_1$-$C_8$, optionally comprising one or more conjugated or non-conjugated double bonds p, in particular, the hydrocarbon-based chain is saturated; said chain is optionally substituted with one or more groups, which may be identical or different, chosen from i) hydroxyl, ii) ($C_1$-$C_2$)alkoxy, iii) (poly)hydroxy($C_2$-$C_4$)alkoxy(di)($C_1$-$C_2$)(alkyl)amino, iv) $R^a$—$Z^a$—C($Z^b$)—$Z^c$—, and v) $R^a$—$Z^a$—S(O)$_t$—$Z^c$— with $Z^a$ and $Z^b$, which may be identical or different, representing an oxygen or sulfur atom, or a group $NR^{a'}$, $Z^c$, representing a bond, an oxygen or sulfur atom, or a group $NR^a$; $R^a$, representing an alkali metal, a hydrogen atom, an alkyl group, or alternatively is absent if another part of the cationic molecule and $R^{a'}$ representing a hydrogen atom or an alkyl group and t is equal to 1 or 2; more particularly, the groups iv) are chosen from carboxylate —C(O)O or —C(O)OMetal (metal=alkali metal), carboxyl —C(O)—OH, guanidino $H_2H$—C($NH_2$)—NH—, amidino $H_2H$—C($NH_2$)—, (thio)ureo $H_2N$—C(O)—NH— and $H_2N$—C(S)—NH—, aminocarbonyl —C(O)—$NR^{a'}_2$ or aminothiocarbonyl —C(S)—$NR^{a'}_2$; carbamoyl $R^{a'}$—C(O)—$NR^{a'}$— or thiocarbamoyl $R^{a'}$—C(S)—NRa'— with Ra', which may be identical or different, representing a hydrogen atom or a ($C_1$-$C_4$) alkyl group;

the "aryl" or "heteroaryl" radicals or the aryl or heteroaryl part of a radical may be substituted with at least one substituent borne by a carbon atom, chosen from:

a $C_1$-$C_{10}$ and preferably $C_1$-$C_8$ alkyl radical optionally substituted with one or more radicals chosen from the following radicals: hydroxyl, $C_1$-$C_2$ alkoxy, (poly)hydroxy($C_2$-$C_4$)alkoxy, acylamino, amino substituted with two identical or different $C_1$-$C_4$ alkyl radicals optionally bearing at least one hydroxyl group, or it being possible for the two radicals to form, with the nitrogen atom to which they are attached, a saturated or unsaturated and optionally substituted 5- to 7-membered and preferably 5- or 6-membered heterocycle optionally comprising another nitrogen or non-nitrogen heteroatom;

a halogen atom;

a hydroxyl group;

a $C_1$-$C_2$ alkoxy radical;

a $C_2$-$C_4$ (poly)hydroxyalkoxy radical;

an amino radical;

a 5- or 6-membered heterocycloalkyl radical;

an optionally cationic 5- or 6-membered heteroaryl radical, preferentially imidazolium, optionally substituted with a ($C_1$-$C_4$)alkyl radical, preferentially methyl;

an amino radical substituted with one or two identical or different $C_1$-$C_6$ alkyl radicals, optionally bearing at least:

i) a hydroxyl group, ii) an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom, iii) a quaternary ammonium group —$N^+$R'R"R"', $M^-$ for which R', R" and R"', which may be identical or different, represent a hydrogen atom or a $C_1$-$C_4$ alkyl group; and $M^-$ represents the counterion of the corresponding organic or mineral acid or of the corresponding halide;

iv) or an optionally cationic 5- or 6-membered heteroaryl radical, preferentially imidazolium, optionally substituted with a ($C_1$-$C_4$)alkyl radical, preferentially methyl;

an acylamino radical (—NR—C(O)—R') in which the radical R is a hydrogen atom or a $C_1$-$C_4$ alkyl radical optionally bearing at least one hydroxyl group and the R' radical is a $C_1$-$C_2$ alkyl radical;

a carbamoyl radical ($(R)_2N$—C(O)—) in which the radicals R, which may be identical or different, represent a hydrogen atom or a $C_1$-$C_4$ alkyl radical optionally bearing at least one hydroxyl group;

an alkylsulfonylamino radical (R'—S$(O)_2$—N(R)—) in which the radical R represents a hydrogen atom or a $C_1$-$C_4$ alkyl radical optionally bearing at least one hydroxyl group and the radical R' represents a $C_1$-$C_4$ alkyl radical or a phenyl radical; an aminosulfonyl radical ($(R)_2N$—S$(O)_2$—) in which the radicals R, which may be identical or different, represent a hydrogen atom or a $C_1$-$C_4$ alkyl radical optionally bearing at least one hydroxyl group;

a carboxylic radical in acid or salified (preferably with an alkali metal or a substituted or unsubstituted ammonium) form;

a cyano group;

a nitro or nitroso group;

a polyhaloalkyl group, preferentially trifluoromethyl;

the cyclic or heterocyclic part of a non-aromatic radical may be substituted with at least one substituent chosen from the following groups:

hydroxyl;

$C_1$-$C_4$ alkoxy or $C_2$-$C_4$ (poly)hydroxyalkoxy;

$C_1$-$C_4$ alkyl;

alkylcarbonylamino (R—C(O)—N(R')—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, optionally bearing at least one hydroxyl group, said alkyl radicals possibly forming, with the nitrogen atom to which they are attached a saturated or unsaturated, optionally substituted 5- to 7-membered heterocycle optionally comprising at least one other nitrogen or non-nitrogen heteroatom;

alkylcarbonyloxy (R—C(O)—O—) in which the radical R is a $C_1$-$C_4$ alkyl radical or an amino group optionally substituted with one or two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl (R-G-C(O)—) in which the radical R is a $C_1$-$C_4$ alkoxy radical, G is an oxygen atom or an amino group optionally substituted with a $C_1$-$C_4$ alkyl group optionally bearing at least one hydroxyl group, said alkyl radical possibly forming with the nitrogen atom to which they are attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

a hydrocarbon-based chain is unsaturated when it includes one or more double bonds and/or one or more triple bonds;

an “aryl” radical represents a fused or non-fused monocyclic or polycyclic carbon-based group comprising from 6 to 22 carbon atoms, and in which at least one ring is aromatic; preferentially, the aryl radical is a phenyl, biphenyl, naphthyl, indenyl, anthracenyl or tetrahydronaphthyl;

a “heteroaryl” group represents an optionally cationic, 5- to 22-membered, monocyclic or fused or non-fused polycyclic group, comprising from 1 to 6 heteroatoms chosen from nitrogen, oxygen, sulfur and selenium, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and the ammonium salt thereof;

a “heterocyclic” group is a 5- to 22-membered, monocyclic or fused or non-fused polycyclic radical that may contain one or more aromatic or non-aromatic unsaturations, including from 1 to 6 heteroatoms chosen from nitrogen, oxygen and sulfur atoms;

a “heterocycloalkyl” radical is a saturated heterocyclic radical such as morpholinyl, piperazinyl or piperidyl;

a “cationic heteroaryl” group is a heteroaryl radical as defined previously that includes an endocyclic or exocyclic quaternized cationic group, when the cationic charge is endocyclic, it is included in the electron delocalization via the mesomeric effect, for example it is a pyridinium, imidazolium or indolinium group:

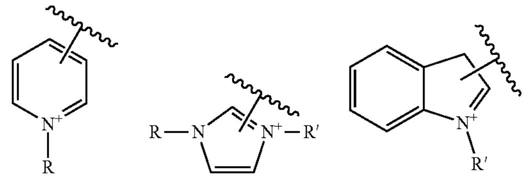

with R and R' being a heteroaryl substituent as defined above and particularly a (hydroxy)($C_1$-$C_8$)alkyl group such as methyl;

when the charge is exocyclic, for example, it is an ammonium or phosphonium substituent $R^+$ such as trimethylammonium, which is exterior to the heteroaryl such as pyridyl, indolyl, imidazolyl or naphthalimidyl in question;

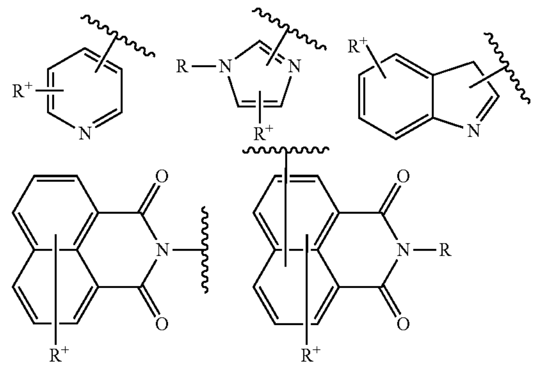

with R a heteroaryl substituent as defined above and $R^+$ an ammonium $R_aR_bR_cN^+$—, phosphonium $R_aR_bR_cP^+$— or ammonium $R_aR_bR_cN^+$—($C_1$-$C_6$)alkylamino group with $R_a$, $R_b$ and $R_c$, which may be identical or different, representing a hydrogen atom or a ($C_1$-$C_8$)alkyl group such as methyl;

a “cationic aryl group bearing an exocyclic charge” is an aryl ring whose quaternized cationic group is exterior to said ring; it is notably an ammonium or phosphonium $R^+$ substituent, such as trimethylammonium, which is exterior to the aryl such as phenyl or naphthyl:

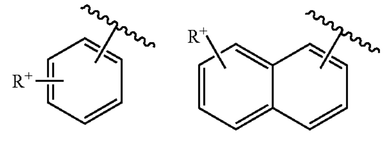

an “alkyl” group is a linear or branched $C_1$-$C_{10}$ and preferably $C_1$-$C_6$ hydrocarbon-based radical;

an “alkenylene radical” is an unsaturated hydrocarbon-based divalent radical as defined previously, which may contain from 1 to 4 conjugated or unconjugated double bonds —C═C—; the alkenylene group particularly contains 1 or 2 unsaturations;

the term “optionally substituted” applied to the alkyl radical implies that said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming with the nitrogen atom that bears them a 5- to 7-membered heterocycle optionally comprising another nitrogen or non-nitrogen heteroatom; v) or a quaternary ammonium group $—N^+R'R''R'''$, $M^-$ for which R', R" and R'", which may be identical or different, represent a hydrogen atom or a $C_1$-$C_4$ alkyl group, or alternatively $—N^+R'R''R'''$ forms a heteroaryl such as imidazolium optionally substituted with a $C_1$-$C_4$ alkyl group, and $M^-$ represents the counterion of the organic or mineral acid or of the corresponding halide;

an "alkoxy radical" is an alkyl-oxy radical for which the alkyl radical is a linear or branched $C_1$-$C_{10}$ and preferentially $C_1$-$C_6$ hydrocarbon-based radical;

when the alkoxy group is optionally substituted, this implies that the alkyl group is optionally substituted as defined hereinabove;

the "tone depth" is the unit known to hairstyling professionals, and published in the book "Science des traitements capillaires [Science of hair treatment]" by Charles ZVIAK 1988, edited by Masson, pages 215 and 278; the tone depths range from 1 (black) to 10 (very light blond), one unit corresponding to one tone, the higher the figure, the lighter the shade;

a "dark" keratin fiber is a keratin fiber whose lightness L* measured in the CIE L*a*b* system is less than or equal to 45 and preferably less than or equal to 40, given that L*=0 is equivalent to black and L*=100 is equivalent to white;

"naturally or artificially dark hair" means hair whose tone depth is less than or equal to 6 (dark blond) and preferably less than or equal to 4 (chestnut-brown). Artificially dyed hair is hair whose color has been modified by a dye treatment, for example dyeing with direct dyes or oxidation dyes;

the term "anionic counterion" refers to an anion or an anionic group derived from an organic or mineral acid salt which counterbalances the cationic charge of the cationic salt; the anionic counterion, derived from the organic or mineral acid salt, ensures the electrical neutrality of the molecule; it is thus understood that when the anion comprises several anionic charges, then the same anion may serve for the electrical neutrality;

moreover, the addition salts that may be used in the context of the invention are notably chosen from addition salts with a cosmetically acceptable base such as the basifying agents as defined below, for instance alkali metal hydroxides such as sodium hydroxide, potassium hydroxide, aqueous ammonia, amines or alkanolamines;

the expression "at least one" is equivalent to "one or more";

the limits of a range of values are included in that range, notably in the expressions "between . . . and . . . " and "ranging from . . . to . . . "; and the expression "inclusive" for a range of concentrations means that the limits of the range are included in the defined interval.

a) Direct Dye:

The term "direct dye" means natural and/or synthetic dyes, other than oxidation dyes. These are dyes that will spread superficially on the fiber. They may be ionic or nonionic, i.e. anionic, cationic, neutral or nonionic. Direct dyes may be of the same types of ionicity or else as mixtures.

According to a particular embodiment of the invention, the direct dyes a) are neutral, cationic or anionic direct dyes chosen from: acridines; acridones; anthranthrones; anthrapyrimidines; anthraquinones; azines; (poly)azos or azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bis-isoindolines; carboxanilides; coumarins; cyanines, such as (di)azacarbocyanines, (di)azahemicyanines, hemicyanines or tetraazacarbocyanines; (di)azines; bis-azines; (di)oxazines; (di)thiazines; (di)phenylamines; (di)phenylmethanes; (di)ketopyrrolopyrroles; flavonoids, such as flavanthrones and flavones; fluorindines; formazans; indamines; indanthrones; indigoids, thioindigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, notably nitro(hetero)aromatics; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazolines; thiazines; thiopyronines; triarylmethanes or xanthenes and natural direct dyes; more preferentially, the direct dyes a) of the invention are chosen from anthraquinones, (poly)azos, azomethines and stilbenes.

The direct dyes a) are in particular chosen from nitrobenzene direct dyes, which are neutral, cationic (or basic dyes) or anionic (or acid dyes), azo direct dyes, which are neutral, cationic (or basic dyes) or anionic (or acid dyes), tetraazapentamethine dyes, which are neutral, cationic (or basic dyes) or anionic (or acid dyes), quinone dyes, which are cationic (or basic dyes) or anionic (or acid dyes) and in particular anthraquinones, which are neutral, cationic (or basic dyes) or anionic (or acid dyes), azine direct dyes, which are neutral, cationic (or basic dyes) or anionic (or acid dyes), triarylmethane direct dyes, which are neutral, cationic (or basic dyes) or anionic (or acid dyes), azomethine direct dyes, which are neutral, cationic (or basic dyes) or anionic (or acid dyes), and natural direct dyes.

More particularly, the direct dyes a) are chosen from azo direct dyes; (poly)methine dyes such as cyanines, hemicyanines and styryl dyes; carbonyl dyes; azine dyes; nitro (hetero)aryl dyes; tri(hetero)arylmethane dyes; porphyrin dyes; phthalocyanine dyes, and natural direct dyes, alone or as mixtures.

The neutral, anionic or cationic direct dyes according to the invention are preferably chosen from the following dyes: acridines; acridones; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines, such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoids, such as flavanthrones and flavones; fluorindines; formazans; indamines; indanthrones; indigoids and pseudoindigoids; indophenols; indoanilines; isoindolines; isoindolinones; isoviolanthrones; lactones; (poly)methines, such as dimethines of stilbene or styryl types; naphthalimides; naphthanilides;

naphtholactams; naphthoquinones; nitro, notably nitro(hetero)aromatics; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazole; thiazines; thioindigos; thiopyronines; triarylmethanes or xanthenes.

Preferentially, the direct dye(s) a) are neutral direct dyes; preferably chosen from the hydrazono dyes of formulae (IIIa) and (III'a), the azo and styryl dyes (IVa), the diazo and distyryl dyes (IV'a) and (IV"a), the anthraquinone dyes (Va) and the azomethine dyes (VIa) and (VI'a) below:

(IIIa)

Ar″—C($R^a$)═N—N($R^b$)—Ar (III'a)

Ar″—N($R^a$)═N—C($R^b$)—Ar (IVa)

Ar—T═T′—Ar″

(IV'a)

Ar″—T═T′—Ar′—T′═T—Ar (IV"a)

Ar—T═T′—L—T′═T—Ar (Va)

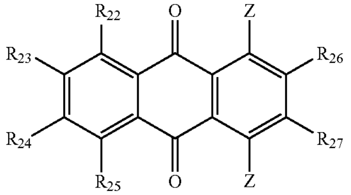

(VIa)

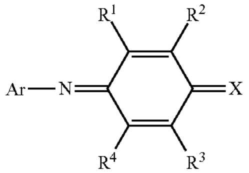

(VI'a)

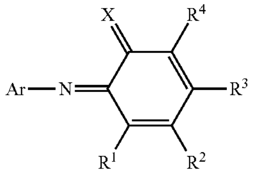

in which formulae (IIIa), (III'a), (IVa), (IV'a), (IV"a), (Va), (VIa) and (VI'a):

Ar represents an aryl radical, such as phenyl or naphthyl, substituted with at least one electron-donating group such as i) optionally substituted ($C_1$-$C_8$)alkyl, ii) optionally substituted ($C_1$-$C_8$)alkoxy, iii) amino, iv) (di)($C_1$-$C_8$)(alkyl)amino optionally substituted on the alkyl group(s) with a hydroxyl group, v) aryl($C_1$-$C_8$)alkylamino, vi) optionally substituted N—($C_1$-$C_8$)alkyl-N-aryl($C_1$-$C_8$)alkylamino or, as a variant, Ar represents a julolidine group;

Ar' represents an optionally substituted divalent (hetero)arylene group such as phenylene, particularly para-phenylene, or naphthalene, which is optionally substituted, preferably with one or more ($C_1$-$C_8$) alkyl, hydroxyl or ($C_1$-$C_8$)alkoxy groups;

Ar" represents a (hetero)aryl radical, which is optionally substituted, preferably with at least i) an electron-withdrawing group such as nitro, nitroso, —C(X)—X'—R' or ii) a (di)($C_1$-$C_6$)(alkyl)amino group, iii) hydroxyl, iv) ($C_1$-$C_6$)alkoxy; (hetero)aryl is particularly chosen from imidazolyl, triazolyl, indolyl or pyridyl or phenyl optionally substituted with at least one group chosen from nitro, nitroso and amino, preferably substituted in the position para to the phenyl group;

X and X', which may be identical or different, represent an oxygen or sulfur atom, or a group NR'", preferably an oxygen atom;

$R_1$, $R^2$, $R^3$ and $R^4$, which may be identical or different, represent a hydrogen or halogen atom, or a group chosen from hydroxyl, thiol, ($C_1$-$C_4$)alkyl, ($C_1$-$C_4$) alkoxy, (di)($C_1$-$C_4$)(alkyl)amino, nitro and nitroso;

R' and R" represent a ($C_1$-$C_4$)alkyl group;

$R^a$ and $R^b$, which may be identical or different, represent a hydrogen atom or a ($C_1$-$C_8$)alkyl group, which is optionally substituted, preferably with a hydroxyl group;

or, as a variant, the substituent $R^a$ with a substituent of Ar" and/or $R^b$ with a substituent of Ar and/or $R^a$ with $R^b$ form, together with the atoms that bear them, a (hetero) cycloalkyl;

particularly, $R^a$ and $R^b$ represent a hydrogen atom or a ($C_1$-$C_4$)alkyl group, which is optionally substituted with a hydroxyl group;

T and T', which may be identical or different, represent a group C($R^a$) or N, preferably N; and L represents a divalent group -ALK-, —C(X)-ALK-, -ALK—C(X)— or —C(X)-ALK-C(X')— with ALK representing a linear or branched ($C_1$-$C_6$)alkylene group, such as methylene and X and X', as defined previously, $R^{22}$, $R^{23}$, $R^{24}$, $R^{25}$, $R^{26}$ and $R^{27}$, which may be identical or different, represent a hydrogen or halogen atom, or a group chosen from:

($C_1$-$C_6$)alkyl;

hydroxyl, mercapto;

($C_1$-$C_6$)alkoxy, ($C_1$-$C_6$)alkylthio;

aryloxy or arylthio;

aryl($C_1$-$C_6$)(alkyl)amino;

(di)($C_1$-$C_6$)(alkyl)amino;

(di)(hydroxy($C_1$-$C_6$)alkyl)amino;

Z' represents a hydrogen atom or a group $NR_{28}R_{29}$ with $R_{28}$ and $R_{29}$, which may be identical or different, representing a hydrogen atom or a group chosen from:

($C_1$-$C_6$)alkyl;

polyhydroxy($C_1$-$C_6$)alkyl such as hydroxyethyl;

aryl optionally substituted with one or more groups, particularly i) ($C_1$-$C_6$)alkyl; iii) $R^o$—C(X)—X'—, $R^o$—X'—C(X)—, $R^o$—X'—C(X)—X"— with $R^o$ representing a ($C_1$-$C_6$)alkyl group, a sulfonate;

cycloalkyl; notably cyclohexyl;

Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined previously.

According to one embodiment, the direct dyes a) are of formula (IV"a), particularly of formula (IV'"a), and also the optical, geometrical or tautomeric isomers thereof, the organic or mineral acid or base salts thereof, and solvates thereof such as hydrates:

(IV'''a)

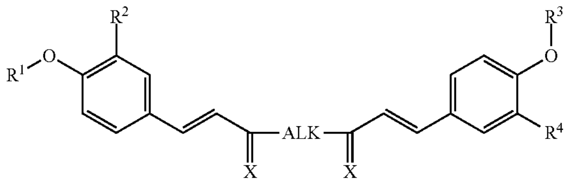

in which formula (IV''''a):

$R_1$ and $R_3$, which may be identical or different, preferably identical, represent a hydrogen atom, a ($C_1$-$C_4$)alkyl group such as methyl or a sugar such as glucosyl, preferably a hydrogen atom;

$R_2$ and $R_4$, which may be identical or different, preferably identical, represent a hydrogen atom, a ($C_1$-$C_4$)alkyl or ($C_1$-$C_4$)alkoxy group or an —O-sugar group such as —O-glucosyl, preferably ($C_1$-$C_4$) alkoxy; such as methoxy;

X, which may be identical or different, preferably identical, represents an oxygen or sulfur atom or N—R with R representing a hydrogen atom, preferably an oxygen atom;

ALK represents a ($C_1$-$C_4$) alkylene group such as methylene or ethylene, preferably methylene.

The dyes of formula (IV''a) may be derived from curcumin, demethoxycurcumin and bis-demethoxycurcumin.

Preferentially, the direct dyes a) of the invention are neutral direct dyes chosen from the azo dyes (IVb), the distyryl dyes (VI''b), the anthraquinone dyes (Vb) and the azomethine dyes (VIb):

(A)

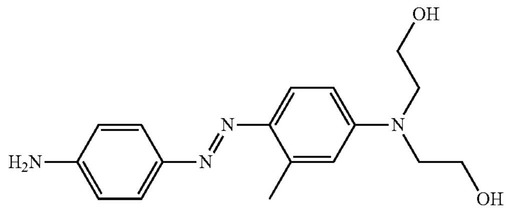

(B)

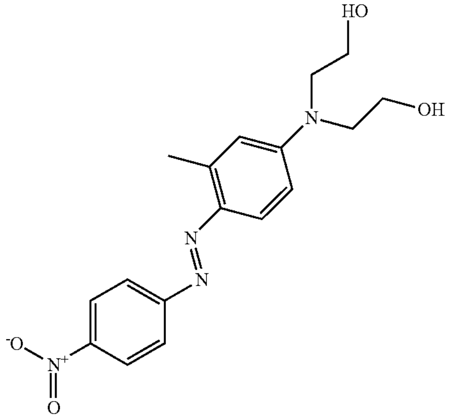

-continued (C)

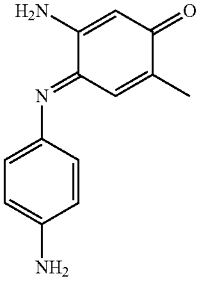

(D)

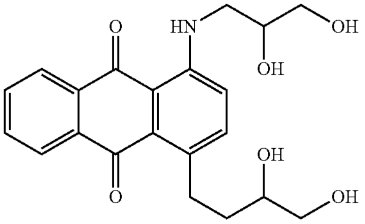

(E)

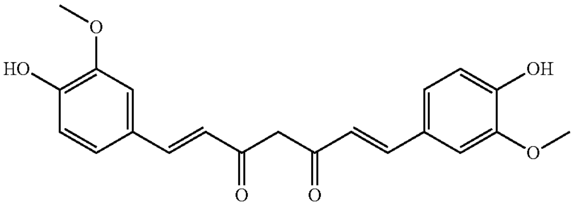

(F)

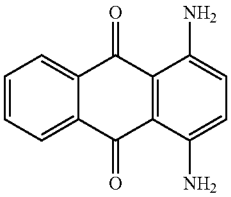

(G)

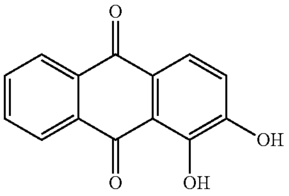

and also the organic or mineral acid or base salts thereof, the optical or geometrical isomers ' ' thereof, and the solvates thereof such as hydrates, preferably chosen from (E) and (G).

According to another particular embodiment of the invention, the direct dyes a) are chosen from cationic direct dyes or dyes commonly referred to as "basic" direct dyes or "basic dyes" on account of their affinity for acidic substances.

For the cationic azo dyes, mention may be made particularly of the cationic dyes described in Kirk-Othmer's Encyclopedia of Chemical Technology, "Dyes, Azo", J. Wiley & Sons, updated on 19 Apr. 2010.

Among the azo dyes that may be used according to the invention, mention may be made of the cationic azo dyes described in patent applications WO 95/15144, WO 95/01772 and EP-714954. According to a particular embodiment of the invention, the direct dye(s) are chosen from cationic dyes known as "basic dyes".

Among the azo dyes described in the Colour Index International 3rd edition, mention may be made notably of the following compounds: Basic Red 22; Basic Red 76; Basic Yellow 57; Basic Brown 16; Basic Brown 17.

Among the cationic quinone dyes, those mentioned in the abovementioned Colour Index International are suitable and, among these, mention may be made, inter alia, of the following dyes: Basic Blue 22; Basic Blue 99.

Among the azine dyes that are suitable for use, mention may be made of those listed in the Colour Index International, for example the following dyes: Basic Blue 17, Basic Red 2.

Among the cationic triarylmethane dyes that may be used according to the invention, mention may be made, in addition to those listed in the Colour Index, of the following dyes: Basic Green 1, Basic Violet 3, Basic Violet 14, Basic Blue 7 and Basic Blue 26.

Mention may also be made of the direct dyes described in U.S. Pat. No. 5,888,252, EP 1 133 975, WO 03/029 359, EP 860 636, WO 95/01772, WO 95/15144 and EP 714 954. Mention may also be made of those listed in the encyclopedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons.

Preferably, the direct dyes are chosen from those resulting from dyes of azo and hydrazono type.

According to a particular embodiment, the direct dyes are cationic azo dyes, described in EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 515 144, GB 1 195 386, U.S. Pat. Nos. 3,524,842, 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

Preferably, the direct dye(s) of the invention comprise a quaternary ammonium group; more preferentially, the cationic charge is endocyclic.

These cationic radicals are, for example, a cationic radical:

- bearing an exocyclic (di/tri)($C_1$-$C_8$)alkylammonium charge, or
- bearing an endocyclic charge, such as comprising a cationic heteroaryl group chosen from: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the hydrazono cationic dyes of formulae (IIb) and (IIIb) and the azo cationic dyes of formulae (IVb) and (Vb) below:

$$\text{Hét}^+—C(R_a)=N—N(R_b)—Ar,\ Q^- \quad \text{(IIb)}$$

$$\text{Hét}^+—N(R_a)—N=C(R_b)—Ar,\ Q^- \quad \text{(IIIb)}$$

$$\text{Hét}^+—N=N—Ar,\ Q^- \quad \text{(IVb)}$$

$$Ar^+—N=N—Ar'',\ Q^- \quad \text{(Vb)}$$

in which formulae (IIb) to (Vb):

- $Het^+$ represents a cationic heteroaryl radical, preferentially bearing an endocyclic cationic charge, such as imidazolium, indolium or pyridinium, which is optionally substituted, preferentially with at least one ($C_1$-$C_8$) alkyl group such as methyl;
- $Ar^+$ represents an aryl radical, such as phenyl or naphthyl, bearing an exocyclic cationic charge, preferentially ammonium, particularly tri($C_1$-$C_8$)alkylammonium, such as trimethylammonium;
- Ar represents an aryl group, notably phenyl, which is optionally substituted, preferentially with one or more electron-donating groups such as i) optionally substituted ($C_1$-$C_8$)alkyl, ii) optionally substituted ($C_1$-$C_8$)alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;
- Ar'' represents an optionally substituted (hetero)aryl group, such as phenyl or pyrazolyl, which are optionally substituted, preferentially by one or more ($C_1$-$C_8$)alkyl, hydroxyl, (di)($C_1$-$C_8$)(alkyl)amino, ($C_1$-$C_8$)alkoxy or phenyl groups; —$R_a$ and $R_b$, which may be identical or different, represent a hydrogen atom or a ($C_1$-$C_8$)alkyl group, which is optionally substituted, preferentially with a hydroxyl group;
- or else the substituent $R_a$ with a substituent of $Het^+$ and/or $R_b$ with a substituent of Ar form, together with the atoms that bear them, a (hetero)cycloalkyl; in particular, $R_a$ and $R_b$ represent a hydrogen atom or a ($C_1$-$C_4$)alkyl group optionally substituted with a hydroxyl group;
- $Q^-$ represents an anionic counterion such as a halide, an alkyl sulfate or an alkylsulfonate.

In particular, mention may be made of the azo and hydrazono direct dyes bearing an endocyclic cationic charge of formulae (Mb) to (Vb) as defined previously. More particularly, the cationic direct dyes of formulae (IIb) to (Vb) bearing an endocyclic cationic charge described in patent applications WO 95/15144, WO 95/01772 and EP 714 954. Preferentially the following direct dyes:

(II-1)

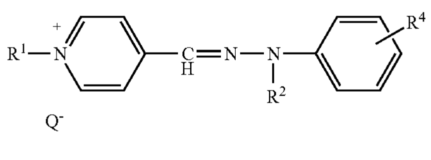

-continued (IV-1)

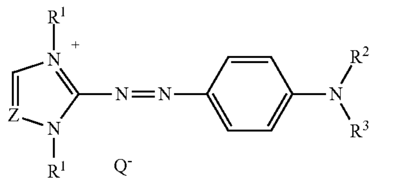

in which formulae (II-1) and (IV-1):

$R_1$ represents a $(C_1\text{-}C_4)$alkyl group such as methyl;

$R_2$ and $R_3$, which may be identical or different, represent a hydrogen atom or a $(C_1\text{-}C_4)$alkyl group, such as methyl; and $R_4$ represents a hydrogen atom or an electron-donating group such as optionally substituted $(C_1\text{-}C_8)$alkyl, optionally substituted $(C_1\text{-}C_8)$alkoxy, or (di)$(C_1\text{-}C_8)$(alkyl)amino optionally substituted on the alkyl group(s) with a hydroxyl group; particularly, $R_4$ is a hydrogen atom, Z represents a CH group or a nitrogen atom, preferentially CH, $Q^-$ is an anionic counterion as defined above, in particular a halide, such as chloride, or an alkyl sulfate, such as methyl sulfate or mesityl.

Particularly, the dyes of formulae (II-1) and (IV-1) are chosen from Basic Red 51, Basic Yellow 87 and Basic Orange 31 or derivatives thereof:

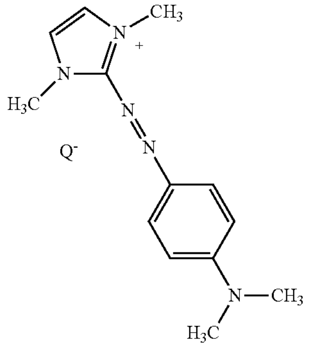

Basic Red 51

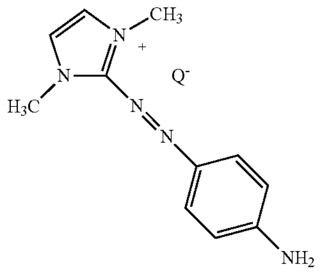

Basic Orange 31

-continued

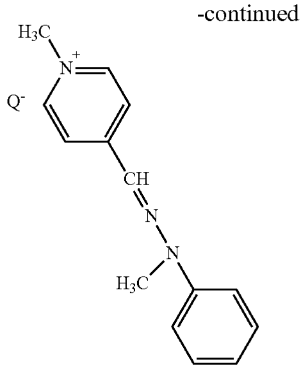

Basic Yellow 87 with Q' being an anionic counterion as defined previously, in particular a halide, such as chloride, or an alkyl sulfate, such as methyl sulfate or mesityl.

According to a particular embodiment of the invention, the direct dyes are fluorescent, i.e. they contain at least one fluorescent chromophore as defined previously.

Fluorescent dyes that may be mentioned include neutral, anionic or cationic dyes chosen from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}borons (BODIPY®), diketopyrrolopyrroles, fluorindines, (poly)methines (in particular cyanines and styryls/hemicyanines), naphthalimides, naphthanilides, naphthylamines (such as dansyls), oxadiazoles, oxazines, perilones, perinones, perylenes, polyenes/carotenoids, squaranes, stilbenes, xanthenes.

Mention may also be made of the fluorescent dyes described in the documents EP 1 133 975, WO 03/029 359, EP 860 636, WO 95/01772, WO 95/15144 and EP 714 954 and those listed in the encyclopedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons, and in the handbook—"A Guide to Fluorescent Probes and Labeling Technologies", 10th Ed., Molecular Probes/Invitrogen—Oregon 2005, circulated on the Internet or in the preceding printed editions.

According to a preferred variant of the invention, the fluorescent dye(s) are cationic polymethines and comprise at least one quaternary ammonium radical, such as those of formula (Vb) below:

$$W^+\text{—}[C(R_c)\text{=}C(R_d)]_{m'}\text{—}Ar,\ Q^- \quad \text{(Vb)}$$

in which formula (Vb):

$W^+$ represents a cationic heterocyclic or heteroaryl group, particularly comprising a quaternary ammonium optionally substituted with one or more $(C_1\text{-}C_8)$alkyl groups, optionally substituted notably with one or more hydroxyl groups;

Ar representing an aryl group such as phenyl or naphthyl, optionally substituted preferentially with i) one or more halogen atoms such as chlorine or fluorine; ii) one or more groups $(C_1\text{-}C_8)$alkyl, preferably of $C_1$-$C_4$ such as methyl; iii) one or more hydroxyl groups; iv) one or more ($C_1$-$C_8$)alkoxy groups such as methoxy; v) one or more hydroxy($C_1$-$C_8$)alkyl groups such as hydroxyethyl, vi) one or more amino groups or (di)($C_1$-$C_8$)alkylamino, preferably with the $C_1$-$C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;

m' represents an integer between 1 and 4 inclusive; in particular, m is 1 or 2; more preferentially 1;

$R_c$ and $R_d$, which may be identical or different, represent a hydrogen atom or an optionally substituted ($C_1$-$C_8$) alkyl group, preferentially of $C_1$-$C_4$, or alternatively $R_c$ contiguous with $W^+$ and/or $R_d$ contiguous with Ar form, with the atoms that bear them, a (hetero)cycloalkyl; particularly, $R_c$ is contiguous with $W^+$ and they form a (hetero)cycloalkyl such as cyclohexyl;

$Q^-$ is an anionic counterion as defined previously.

According to a preferred embodiment of the invention, the direct dyes a) are chosen from anionic direct dyes or dyes commonly referred to as "acidic" direct dyes on account of their affinity for alkaline substances. The term "anionic direct dye" means any direct dye including in its structure at least one $CO_2R$ or $SO_3R$ substituent with R denoting a hydrogen atom or a cation originating from a metal or an amine, or an ammonium ion. The anionic dyes may be chosen from direct nitro acid dyes, azo acid dyes, azine acid dyes, triarylmethane acid dyes, indoamine acid dyes, anthraquinone acid dyes, indigoid dyes and natural acid dyes; preferably, the direct dyes a) are acidic anthraquinone dyes.

As acid dyes according to the invention, mention may be made of the dyes of formulae (III), (III'), (IV), (IV'), (V), (V'), (VI), (VI'), (VII), (VIII), (IX) and (X) below:

a) the diaryl anionic azo dyes of formula (III) or (III'):

(III)

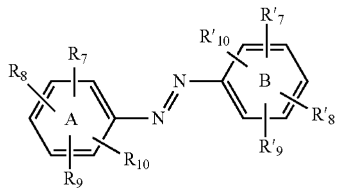

(III')

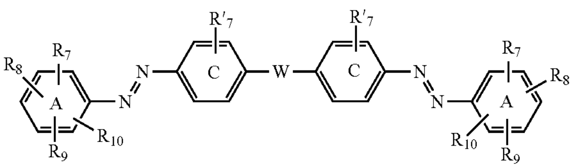

in which formulae (III) and (III'):

$R_7$, $R_8$, $R_9$, $R_{10}$, $R'_7$, $R'_8$, $R'_9$ and $R'_{10}$, which may be identical or different, represent a hydrogen atom or a group chosen from:

($C_1$-$C_6$)alkyl;

($C_1$-$C_6$)alkoxy, ($C_1$-$C_6$)alkylthio;

hydroxyl, mercapto;

nitro, nitroso;

$R^o$—C(X)—X'—, $R^o$—X'—C(X)—, $R^o$—X'—C(X)—X"— with $R^o$ representing a hydrogen atom or a ($C_1$-$C_6$)alkyl or aryl group such as phenyl; X, X' and X", which may be identical or different, representing an oxygen or sulfur atom, or NR with R representing a hydrogen atom or a ($C_1$-$C_6$)alkyl group;

$(O)_2S(O^-)$—, $M^+$ with $M^+$ representing a hydrogen atom or a cationic counterion;

$(O)CO^-$—, $M^+$ with $M^+$ as defined previously;

R"—$S(O)_2$—, with R" representing a hydrogen atom, an alkyl group, or an aryl, (di)($C_1$-$C_6$)(alkyl)amino or aryl($C_1$-$C_6$)(alkyl)amino group; preferentially a phenylamino or phenyl group;

R'"—$S(O)_2$—X'— with R'" representing a ($C_1$-$C_6$) alkyl group or an aryl group which is optionally substituted, X' as defined previously;

(di)($C_1$-$C_6$)(alkyl)amino;

aryl($C_1$-$C_6$)(alkyl)amino optionally substituted with one or more groups chosen from i) nitro; ii) nitroso; iii) $(O)_2S(O^-)$—, $M^+$ and iv) ($C_1$-$C_6$)alkoxy with $M^+$ as defined previously;

optionally substituted heteroaryl; preferentially a benzothiazolyl group;

cycloalkyl; notably cyclohexyl;

Ar—N═N— with Ar representing an optionally substituted aryl group; preferentially a phenyl optionally substituted with one or more alkyl, $(O)_2S(O^-)$—, $M^+$ or phenylamino groups;

or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; x) Ar—N═N— and xi) optionally substituted aryl($C_1$-$C_6$)(alkyl)amino; with $M^+$, $R^o$, X, X', X" and Ar as defined previously;

W represents a sigma bond σ, an oxygen or sulfur atom, or a divalent radical i) —NR— with R as defined previously, or ii) methylene —C($R_a$)($R_b$)— with $R_a$ and $R_b$, together which may be identical or different, representing a hydrogen atom or an aryl group, or alternatively $R_a$ and $R_b$ form, together with the carbon atom that bears them, a spiro cycloalkyl; preferentially, W represents a sulfur atom or $R_a$ and $R_b$ together form a cyclohexyl;

it being understood that formulae (III) and (III') comprise at least one sulfonate radical $(O)_2S(O)$—, $M^+$ or one carboxylate radical $(O)CO^-$—, $M^+$ on one of the rings A, A', B, B' or C; preferentially sodium sulfonate.

As examples of dyes of formula (III), mention may be made of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Food yellow 3 or Sunset Yellow;

and as examples of dyes of formula (III'), mention may be made of: Acid Red 111, Acid Red 134, Acid Yellow 38;

b) the pyrazolone anionic azo dyes of formulae (IV) and (IV'):

(IV)

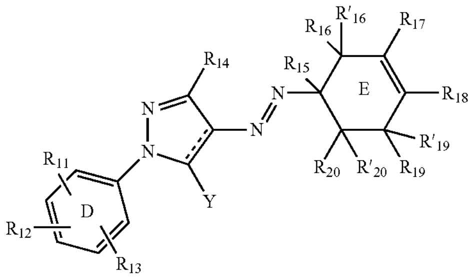

(IV')

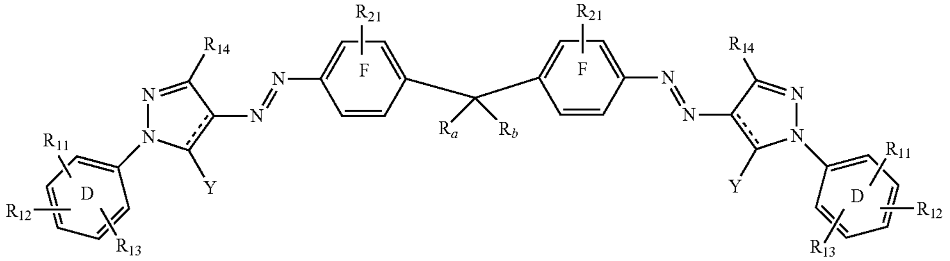

in which formulae (IV) and (IV'):

$R_{11}$, $R_{12}$ and $R_{13}$, which may be identical or different, represent a hydrogen or halogen atom, a $(C_1\text{-}C_6)$alkyl group or —$(O)_2S(O^-)$, $M^+$ with $M^+$ as defined previously;

$R_{14}$ represents a hydrogen atom, a $(C_1\text{-}C_6)$alkyl group or a —$C(O)O^-$, $M^+$ group with $M^+$ as defined previously;

$R_{15}$ represents a hydrogen atom;

$R_{16}$ represents an oxo group, in which case $R'_{16}$ is absent, or alternatively $R_{15}$ with $R_{16}$ together form a double bond;

$R_{17}$ and $R_{18}$, which may be identical or different, represent a hydrogen atom or a group chosen from:

$(O)_2S(O^-)$—, $M^+$ with $M^+$ as defined previously;

Ar—O—$S(O)_2$— with Ar representing an optionally substituted aryl group, preferentially a phenyl optionally substituted with one or more alkyl groups;

$R_{19}$ and $R_{20}$ together form either a double bond, or a benzo group D', which is optionally substituted;

$R'_{16}$, $R'_{19}$ and $R'_{20}$, which may be identical or different, represent a hydrogen atom or a $(C_1\text{-}C_6)$alkyl or hydroxyl group;

$R_{21}$ represents a hydrogen atom or a $(C_1\text{-}C_6)$alkyl or $(C_1\text{-}C_6)$alkoxy group;

$R_a$ and $R_b$, which may be identical or different, are as defined previously; preferentially, $R_a$ represents a hydrogen atom and $R_b$ represents an aryl group such as phenyl;

Y represents either a hydroxyl group or an oxo group;

$\overline{\text{- - - -}}$ represents a single bond when Y is an oxo group; and represents a double bond when Y represents a hydroxyl group;

it being understood that formulae (IV) and (IV') comprise at least one sulfonate radical $(O)_2S(O)$—, $M^+$ or one carboxylate radical $C(O)O$—, $M^+$ on one of the rings D or E; preferentially sodium sulfonate;

As examples of dyes of formula (IV), mention may be made of: Acid Red 195, Acid Yellow 23, Acid Yellow 27, Acid Yellow 76, and as examples of dyes of formula (IV'), mention may be made of: Acid Yellow 17;

c) the anthraquinone dyes of formulae (V) and (V'):

(V)

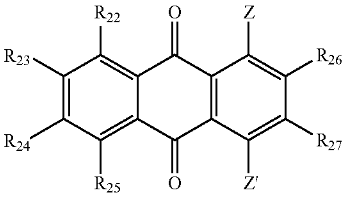

(V')

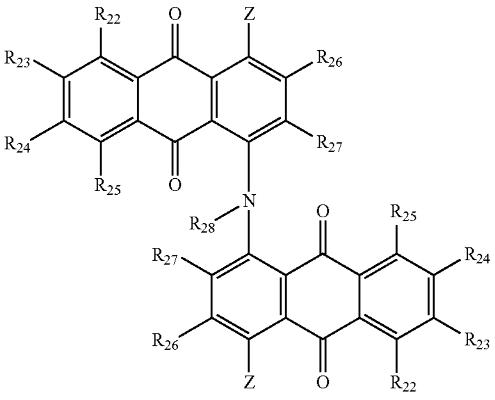

in which formulae (V) and (V'):

$R_{22}$, $R_{23}$, $R_{24}$, $R_{25}$, $R_{26}$ and $R_{27}$, which may be identical or different, represent a hydrogen or halogen atom, or a group chosen from:

$(C_1\text{-}C_6)$alkyl;

hydroxyl, mercapto;

$(C_1\text{-}C_6)$alkoxy, $(C_1\text{-}C_6)$alkylthio;

optionally substituted aryloxy or arylthio, preferentially substituted with one or more groups chosen from alkyl and $(O)_2S(O^-)$—, $M^+$ with $M^+$ as defined previously;

aryl($C_1$-$C_6$)(alkyl)amino optionally substituted with one or more groups chosen from alkyl and $(O)_2S(O^-)$—, $M^+$ with $M^+$ as defined previously;

(di)($C_1$-$C_6$)(alkyl)amino;

(di)(hydroxy($C_1$-$C_6$)alkyl)amino;

$(O)_2S(O^-)$—, $M^+$ with $M^+$ as defined previously;

Z' represents a hydrogen atom or a group $NR_{28}R_{29}$ with $R_{28}$ and $R_{29}$, which may be identical or different, representing a hydrogen atom or a group chosen from:

($C_1$-$C_6$)alkyl;

polyhydroxy($C_1$-$C_6$)alkyl such as hydroxyethyl;

aryl optionally substituted with one or more groups, particularly i) ($C_1$-$C_6$)alkyl such as methyl, n-dodecyl, n-butyl; ii) $(O)_2S(O^-)$—, $M^+$ with $M^+$ as defined previously; iii) $R^o$—C(X)—X'—, $R^o$—X'—C(X)—, $R^o$—X'—C(X)—X"— with $R^o$, X, X' and X" as defined previously, preferentially $R^o$ represents a ($C_1$-$C_6$)alkyl group;

cycloalkyl; notably cyclohexyl;

Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined previously;

it being understood that formulae (V) and (V') comprise at least one sulfonate radical $(O)_2S(O^-)$—, $M^+$ or one carboxylate radical —C(O)$O^-$, $M^+$; preferentially sodium sulfonate;

As examples of dyes of formula (V), mention may be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; EXT violet No. 2; and as examples of dyes of formula (V'), mention may be made of: Acid Black 48;

d) the nitro dyes of formulae (VI) and (VI'):

(VI)

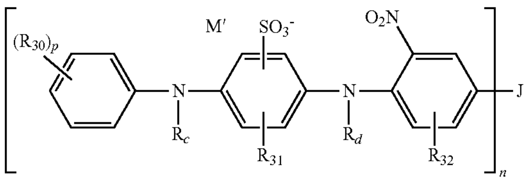

(VI')

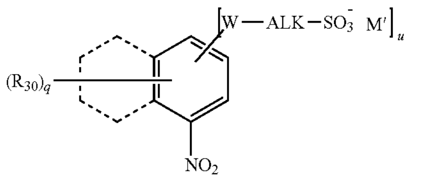

in which formulae (VI) and (VI'):

$R_{30}$, $R_{31}$ and $R_{32}$, which may be identical or different, represent a hydrogen or halogen atom, or a group chosen from:

($C_1$-$C_6$)alkyl;

($C_1$-$C_6$)alkoxy optionally substituted with one or more hydroxyl groups, ($C_1$-$C_6$)alkylthio optionally substituted with one or more hydroxyl groups;

hydroxyl, mercapto;

nitro, nitroso;

polyhalo($C_1$-$C_6$)alkyl;

$R^o$—C(X)—X'—, $R^o$—X'—C(X)—, $R^o$—X'—C(X)—X"— with $R^o$, X, X' and X" as defined previously;

$(O)_2S(O^-)$—, $M^+$ with $M^+$ as defined previously;

(O)C$O^-$—, $M^+$ with $M^+$ as defined previously;

(di)($C_1$-$C_6$)(alkyl)amino;

(di)(hydroxy($C_1$-$C_6$)alkyl)amino;

heterocycloalkyl such as piperidino, piperazino or morpholino;

in particular, $R_{30}$, $R_{31}$ and $R_{32}$ represent a hydrogen atom;

$R_c$ and $R_d$, which may be identical or different, represent a hydrogen atom or a ($C_1$-$C_6$)alkyl group;

W is as defined previously; W particularly represents an —N(H)— group;

ALK represents a linear or branched divalent $C_1$-$C_6$ alkylene group; in particular, ALK represents a —$CH_2$—$CH_2$— group;

n is 1 or 2;

p represents an integer between 1 and 5 inclusive;

q represents an integer between 1 and 4 inclusive;

u is 0 or 1;

when n is 1, J represents a nitro or nitroso group; particularly nitro;

when n is 2, J represents an oxygen or sulfur atom, or a divalent radical —$S(O)_m$— with m representing an integer 1 or 2; preferentially, J represents an —$SO_2$— radical;

M' represents a hydrogen atom or a cationic counterion;

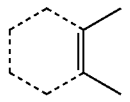, which may be present or absent, represents a benzo group optionally substituted with one or more groups $R_{30}$ as defined previously;

it being understood that formulae (VI) and (VI') comprise at least one sulfonate radical $(O)_2S(O^-)$—, $M^+$ or one carboxylate radical —C(O)$O^-$, $M^+$; preferentially sodium sulfonate;

As examples of dyes of formula (VI), mention may be made of: Acid Brown 13 and Acid Orange 3; as examples of dyes of formula (VI'), mention may be made of: Acid Yellow 1, the sodium salt of 2,4-dinitro-1-naphthol-7-sulfonic acid, 2-piperidino-5-nitrobenzenesulfonic acid, 2-(4'-N,N-(2"-hydroxyethyl)amino-2'-nitro)anilineethanesulfonic acid, 4-p-hydroxyethylamino-3-nitrobenzenesulfonic acid; EXT D&C Yellow 7;

(VII)

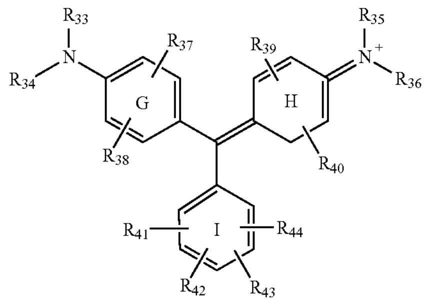

d) the triarylmethane dyes of formula (VII):

in which formula (VII):

$R_{33}$, $R_{34}$, $R_{35}$ and $R_{36}$, which may be identical or different, represent a hydrogen atom or a group chosen from ($C_1$-$C_6$)alkyl, optionally substituted aryl and optionally substituted aryl($C_1$-$C_6$)alkyl; particularly a ($C_1$-$C_6$)alkyl group and benzyl optionally substituted with an $(O)_mS(O^-)$—, $M^+$ group with $M^+$ and m as defined previously;

$R_{37}$, $R_{38}$, $R_{39}$, $R_{40}$, $R_{41}$, $R_{42}$, $R_{43}$ and $R_{44}$, which may be identical or different, represent a hydrogen atom or a group chosen from:

($C_1$-$C_6$)alkyl;

($C_1$-$C_6$)alkoxy, ($C_1$-$C_6$)alkylthio;

(di)($C_1$-$C_6$)(alkyl)amino;

hydroxyl, mercapto;

nitro, nitroso;

$R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or a ($C_1$-$C_6$)alkyl group;

$(O)_2S(O^-)$—, $M^+$ with $M^+$ representing a hydrogen atom or a cationic counterion;

$(O)CO^-$—, $M^+$ with $M^+$ as defined previously;

or alternatively two contiguous groups $R_{41}$ with $R_{42}$ or $R_{42}$ with $R_{43}$ or $R_{43}$ with $R_{44}$ together form a fused benzo group optionally substituted with one or more groups chosen from i) nitro; ii) nitroso; iii) $(O)_2S(O^-)$—, $M^+$; iv) hydroxyl; v) mercapto; vi) (di)($C_1$-$C_6$)(alkyl)amino; vii) $R^o$—C(X)—X'—; viii) $R^o$—X'—C(X)—; ix) $R^o$—X'—C(X)—X"—; with $M^+$, $R^o$, X, X' and X" as defined previously;

particularly, $R_{37}$ to $R_{40}$ represent a hydrogen atom, and $R_{41}$ to $R_{44}$, which may be identical or different, represent a hydroxyl group or $(O)_2S(O^-)$—, $M^+$; and when $R_{43}$ with $R_{44}$ together form a benzo group, it is preferentially substituted with an $(O)_2S(O^-)$— group;

it being understood that at least one of the rings G, H, I or I' comprises at least one sulfonate radical $(O)_2S(O^-)$— or a carboxylate radical —$C(O)O^-$; preferentially sulfonate;

As examples of dyes of formula (VII), mention may be made of: Acid Blue 1; Acid Blue 3; Acid Blue 7, Acid Blue 9; Acid Violet 49; Acid Green 3; Acid Green 5 and Acid Green 50;

e) the xanthene-based dyes of formula (VIII):

(VIII)

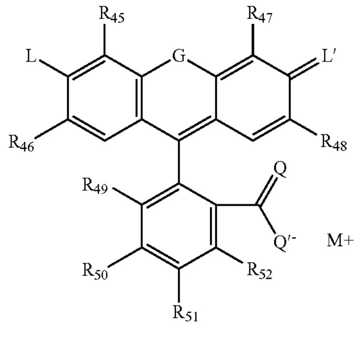

in which formula (VIII):

$R_{45}$, $R_{46}$, $R_{47}$ and $R_{48}$, which may be identical or different, represent a hydrogen or halogen atom;

$R_{49}$, $R_{50}$, $R_{51}$ and $R_{52}$, which may be identical or different, represent a hydrogen or halogen atom, or a group chosen from:

($C_1$-$C_6$)alkyl;

($C_1$-$C_6$)alkoxy, ($C_1$-$C_6$)alkylthio;

hydroxyl, mercapto;

nitro, nitroso;

$(O)_2S(O^-)$—, $M^+$ with $M^+$ representing a hydrogen atom or a cationic counterion;

$(O)CO^-$—, $M^+$ with $M^+$ as defined previously;

particularly, $R_{53}$, $R_{54}$, $R_{55}$ and $R_{48}$ represent a hydrogen or halogen atom;

G represents an oxygen or sulfur atom or a group $NR_e$ with $R_e$ as defined previously; particularly, G represents an oxygen atom;

L represents an alkoxide $O^-$, $M^+$; a thioalkoxide $S^-$, $M^+$ or a group $NR_f$, with $R_f$ representing a hydrogen atom or a ($C_1$-$C_6$)alkyl group, and $M^+$ as defined previously; $M^+$ is particularly sodium or potassium;

L' represents an oxygen or sulfur atom or an ammonium group: $N^+R_fR_g$, with $R_f$ and $R_g$, which may be identical or different, representing a hydrogen atom, a ($C_1$-$C_6$) alkyl group or an optionally substituted aryl group; L' represents particularly an oxygen atom or a phenylamino group optionally substituted with one or more alkyl or $(O)_mS(O^-)$—, $M^+$ groups with m and $M^+$ as defined previously;

Q and Q', which may be identical or different, represent an oxygen or sulfur atom; particularly Q and Q' represent an oxygen atom;

$M^+$ is as defined previously;

As an example of dyes of formula (VIII), mention may be made of: Acid Yellow 73; Acid Red 51; Acid Red 52; Acid Red 87; Acid Red 92; Acid Red 95; Acid Violet 9;

f) the indole-based dyes of formula (IX):

(IX)

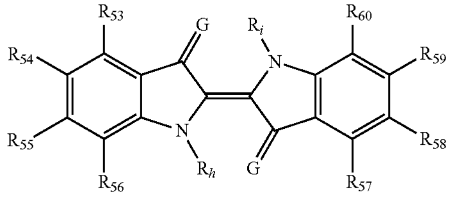

in which formula (IX):

$R_{53}$, $R_{54}$, $R_{55}$, $R_{56}$, $R_{57}$, $R_{58}$, $R_{59}$ and $R_{60}$, which may be identical or different, represent a hydrogen atom or a group chosen from:

($C_1$-$C_6$)alkyl;

($C_1$-$C_6$)alkoxy, ($C_1$-$C_6$)alkylthio;

hydroxyl, mercapto;

nitro, nitroso;

$R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or a ($C_1$-$C_6$)alkyl group;

$(O)_2S(O^-)$—, $M^+$ with $M^+$ representing a hydrogen atom or a cationic counterion;

$(O)CO^-$—, $M^+$ with $M^+$ as defined previously;

G represents an oxygen or sulfur atom or a group $NR_e$ with $R_e$ as defined previously; particularly, G represents an oxygen atom;

$R_i$ and $R_h$, which may be identical or different, represent a hydrogen atom or a ($C_1$-$C_6$)alkyl group;

it being understood that formula (IX) comprises at least one sulfonate radical $(O)_2S(O^-)$—, $M^+$ or one carboxylate radical —$C(O)O^-$, $M^+$; preferentially sodium sulfonate As examples of dyes of formula (IX), mention may be made of: Acid Blue 74.

g) the quinoline-based dyes of formula (X):

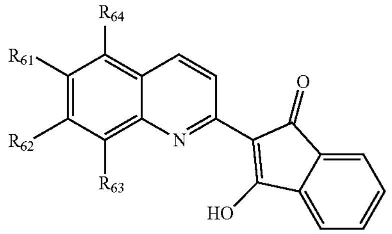

(X)

in which formula (X):

$R_{61}$ represents a hydrogen or halogen atom or a $(C_1-C_6)$ alkyl group;

$R_{62}$, $R_{63}$ and $R_{64}$, which may be identical or different, represent a hydrogen atom or a group $(O)_2S(O^-)$—, $M^+$ with $M^+$ representing a hydrogen atom or a cationic counterion;

or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;

it being understood that formula (X) comprises at least one sulfonate radical $(O)_2S(O^-)$—, $M^+$ preferentially sodium sulfonate.

As examples of dyes of formula (X), mention may be made of: Acid Yellow 2, Acid Yellow 3 and Acid Yellow 5.

More particularly, the dyes of formulae (III) to (VIII) that are useful in the invention are chosen from:

TABLE 1

| | |
|---|---|
| (C.I. 45380) | Acid Red 87 (VIII) |
| (C.I. 10316) | Sodium salt of 2,4-dinitro-1-naphthol-7-sulfonic acid (VI') |
| (C.I. 10383) | Acid Orange 3 (VI) |
| (C.I. 13015) | Acid Yellow 9/Food Yellow 2 (III) |
| (C.I. 14780) | /Direct Red 45/Food Red 13 (III) |
| (C.I. 13711) | Acid Black 52 (III) |
| (C.I. 13065) | Acid Yellow 36 (III) |
| (C.I. 14700) | Sodium salt of 1-hydroxy-2-(2',4'-xylyl-5-sulfonatoazo)naphthalene-4-sulfonic acid/Food Red 1 (III) |
| (C.I. 14720) | Acid Red 14/Food Red 3/Mordant Blue 79 (III) |
| (C.I. 14805) | Sodium salt of 4-hydroxy-3-[(2-methoxy-5-nitrophenyl)diaza]-6-(phenylamino)naphthalene-2-sulfonic acid/Acid Brown 4 (III) |
| (C.I. 15510) | Acid Orange 7/Pigment Orange 17/Solvent Orange 49 (III) |
| (C.I. 15985) | Food Yellow 3/Pigment Yellow 104 (III) |
| (C.I. 16185) | Acid Red 27/Food Red 9 (III) |
| (C.I. 16230) | Acid Orange 10/Food Orange 4(III) |
| (C.I. 16250) | Acid Red 44 (III) |
| (C.I. 17200) | Acid Red 33/Food Red 12 (III) |
| (C.I. 15685) | Acid Red 184 (III) |
| (C.I. 19125) | Acid Violet 3 (III) |
| (C.I. 18055) | Sodium salt of 1-hydroxy-2-(4'-acetamidophenylazo)-8-acetamidonaphthalene-3,6-disulfonic acid/Acid Violet 7/Food Red 11 (III) |
| (C.I. 18130) | Acid Red 135 (III) |
| (C.I. 19130) | Acid Yellow 27 (IV) |
| (C.I. 19140) | Acid Yellow 23/Food Yellow 4 (IV) |
| (C.I. 20170) | 4'-(Sulfonato-2",4"-dimethyl)bis(2,6-phenylazo)-1,3-dihydroxybenzene/Acid Orange 24 (III) |
| (C.I. 20470) | Sodium salt of 1-amino-2-(4'-nitrophenylazo)-7-phenylazo-8-hydroxynaphthalene-3,6-disulfonic acid/Acid Black 1 (III) |
| (C.I. 23266) | (4-((4-methylphenyl)sulfonyloxy)phenylazo)-2,2'-dimethyl-4-((2-hydroxy-5,8-disulfonato)naphthylazo)biphenyl/Acid Red 111 (III') |
| (C.I. 27755) | Food Black 2 (III) |
| (C.I. 25440) | 1-(4'-Sulfonatophenylazo)-4-((2"-hydroxy-3"-acetylamino-6",8"-disulfonato)naphthylazo)-6-sulfonatonaphthalene (tetrasodium salt)/Food Black 1 (III) |
| (C.I. 42090) | Acid Blue 9 (VII) |
| (C.I. 60730) | Acid Violet 43 (V) |
| (C.I. 61570) | Acid Green 25 (V) |
| (C.I. 62045) | Sodium salt of 1-amino-4-cyclohexylamino-9,10-anthraquinone-2-sulfonic acid/Acid Blue 62 (V) |
| (C.I. 62105) | Acid Blue 78 (V) |
| (C.I. 14710) | Sodium salt of 4-hydroxy-3-((2-methoxyphenyl)azo)-1-naphthalenesulfonic acid/Acid Red 4 (III) |
| | 2-Piperidino-5-nitrobenzenesulfonic acid (VI') |
| | 2-(4'-N,N-(2"-Hydroxyethyl)amino-2'-nitro)anilineethanesulfonic acid (VI') |
| | 4-β-Hydroxyethylamino-3-nitrobenzenesulfonic acid (VI') |

TABLE 1-continued

| | |
|---|---|
| (C.I. 42640) | Acid Violet 49 (VII) |
| (C.I. 42080) | Acid Blue 7 (VII) |
| (C.I. 58005) | Sodium salt of 1,2-dihydroxy-3-sulfoanthraquinone/Mordant Red 3 (V) |
| (C.I. 62055) | Sodium salt of 1-amino-9,10-dihydro-9,10-dioxo-4-(phenylamino) 2-anthracenesulfonic acid/Acid Blue 25 (V) |
| (C.I. 14710) | Sodium salt of 4-hydroxy-3-((2-methoxyphenyl)azo)-1-naphthalenesulfonic acid/ Acid Red 4 (III) |

Most of these dyes are described in particular in the Color Index published by The Society of Dyers and Colorists, P.O. Box 244, Perkin House, 82 Grattan Road, Bradford, Yorkshire, BD1 2LU England.

The anionic dyes that are most particularly preferred are the dyes designated in the Color Index under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl)amino]-5-methylbenzenesulfonic acid), C.I. 15510 (monosodium salt of 4-[(2-hydroxy-1-naphthalenyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxy-3,6-naphthalenedisulfonic acid), C.I. 42090 (disodium salt of N-ethyl-N-[4-[[4-[ethyl(3-sulfophenyl)methyl]amino]phenyl](2-sulfophenyl)methylene]-2,5-cyclohexadien-1-ylidene]-3-sulfobenzenemethanaminium hydroxide, inner salt), C.I. 61570 (disodium salt of 2,2'-[(9,10-dihydro-9,10-dioxo-1,4-anthracenediyl)diimino]bis[5-methyl]benzenesulfonic acid).

Use may also be made of compounds corresponding to the mesomeric or tautomeric forms of structures (III) to (X).

Preferably, the anionic direct dye(s) of the invention are chosen from the dyes of formula (V) such as Acid Violet 43.

The anionic direct dye(s) particularly represent from 0.001% to 20% by weight approximately relative to the total weight of the composition, and preferentially from 0.005% to 10% by weight approximately. More particularly, the anionic dye(s) represent from 0.01% to 5% by weight.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin, orceins, brazilin, brazilein, hematin and hematoxylin. Extracts or decoctions containing these natural dyes and notably henna-based poultices or extracts may also be used.

Preferably, the direct dye(s) a) have a solubility in water at a temperature of 22° C. and at atmospheric pressure (760 mmHg, i.e. $1.013\times10^5$ Pa) of less than 5% by weight, more preferentially less than 1% by weight and even more preferentially less than 0.5% by weight.

The direct dye(s) a) advantageously represent from 0.001% to 10% by weight, preferentially from 0.05% to 5% by weight relative to the total weight of the composition comprising them, more preferentially from 0.3% to 3% by weight relative to the total weight of the composition comprising them.

a) Unsaturated Heterocyclic Salts of Formula (A):

The second ingredient b) used in the process and the composition of the invention is an unsaturated heterocyclic salt of formula (A) as defined previously.

According to a particular embodiment of the invention, the salt(s) of formula (A) are chosen from those of formulae (I) and (II) below, and also the tautomeric forms thereof:

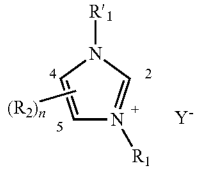
(I)

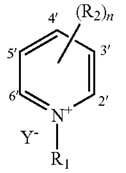
(II)

in which formulae (I) and (II):

$R_1$ represents a linear or branched, saturated or unsaturated $(C_1\text{-}C_{12})$ hydrocarbon-based group optionally substituted with one or more groups chosen from hydroxyl, amino, $(C_1\text{-}C_6)$dialkylamino, $(C_1\text{-}C_6)$alkylamino, carboxyl, carboxylate, carbamide, $(C_1\text{-}C_4)$ alkoxy, —$SO_3H$, sulfonate and phenyl;

$R'_1$ represents a hydrogen atom, a linear or branched, saturated or unsaturated $(C_1\text{-}C_{12})$ hydrocarbon-based group optionally substituted with one or more groups chosen from hydroxyl, amino, $(C_1\text{-}C_6)$dialkylamino, $(C_1\text{-}C_6)$alkylamino, carboxyl, carboxylate, carbamide, $(C_1\text{-}C_4)$alkoxy, —$SO_3H$, sulfonate and phenyl; and $R_2$ represents a hydroxyl group, a linear or branched, saturated or unsaturated $(C_1\text{-}C_{12})$ hydrocarbon-based group optionally substituted with one or more groups chosen from hydroxyl, $(C_1\text{-}C_4)$alkoxy, —$SO_3H$, sulfonate and benzene;

n is 0, 1, 2 or 3; preferably, n is 0 or 1;

Y' represents an anionic counterion;

it being understood that:

when one of the hydrocarbon-based groups of $R_1$, $R'_1$ or $R_2$ is substituted with a carboxylate or sulfonate group, then $Y^-$ is absent to ensure the electrical neutrality of the salt of formula (A), and when n is equal to 2 or 3, then the substituents are identical or different.

According to a particular embodiment of the invention, the salts of formulae (A), (I) and (II) are such that $R_1$ represents a linear or branched, preferably linear, saturated or unsaturated $(C_1\text{-}C_{10})$ hydrocarbon-based group, optionally substituted with one or more groups chosen from hydroxyl, $(C^1C_4)$alkoxy, —$SO_3H$, —$SO_3^-$ and phenyl; preferentially, $R_1$ represents a linear or branched $(C_1\text{-}C_8)$alkyl group. More preferentially, $R_1$ represents a linear $(C_1\text{-}C_8)$ alkyl group, optionally substituted with one or more hydroxyl, phenyl, —$SO_3H$ and —$SO_3^-$ groups, or alternatively $R_1$ represents a linear or branched ($C_2$-$C_6$)alkenyl group, preferably vinyl or allyl.

According to a particular embodiment, the salt(s) of formula (I) are such that $R'_1$ represents a hydrogen atom or a linear or branched, saturated or unsaturated ($C_1$-$C_8$) hydrocarbon-based group optionally substituted with one or more groups chosen from hydroxyl, ($C_1$-$C_2$)alkoxy, —$SO_3H$, —$SO_3^-$ and phenyl. Preferentially, $R'_1$ represents a hydrogen atom or a linear or branched, more preferentially linear, saturated ($C_1$-$C_6$) hydrocarbon-based group, particularly methyl.

According to a particular embodiment, the salt(s) of formula (I) are such that $R_2$ represents a linear or branched, saturated ($C_1$-$C_6$) hydrocarbon-based group such as methyl; preferably, n is 1 and $R_2$ is in position 2.

According to a particular embodiment, the salt(s) of formula (II) are such that $R_1$ represents a linear or branched, saturated or unsaturated ($C_1$-$C_{12}$) hydrocarbon-based group; in particular, $R_1$ represents a linear or branched ($C_1$-$C_8$)alkyl group, preferably, $R_1$ represents a ($C_1$-$C_4$)alkyl group such as methyl.

According to a particular embodiment, the salts of formula (II) are such that $R_2$ represents a hydroxyl group, a linear or branched, saturated or unsaturated ($C_1$-$C_{12}$) hydrocarbon-based group, optionally substituted with one or more hydroxyl, ($C_1$-$C_4$)alkoxy, —$SO_3H$, —$SO_3^-$ and phenyl groups; preferentially, $R_2$ represents a hydroxyl group or a ($C_1$-$C_4$)alkyl group such as methyl; $R_2$ is preferably positioned in position 2', 3' or 4'.

According to a particular embodiment, the salt(s) of formula (A), (I) or (II) in which $Y^-$ represents an anionic counterion chosen from i) halides such as chloride, bromide, ii) hydrogen sulfates, iii) (bis)(poly)halo($C_1$-$C_{12}$)(alkyl) sulfonylimides such as bis(trifluoromethylsulfonyl)imide and bis(fluorosulfonyl)imide, iv) ($C_1$-$C_{12}$)alkyl sulfates, v) (poly)halophosphates such as hexafluorophosphate, vi) ($C_1$-$C_{12}$)(alkyl)phosphates, phosphate, vii) (poly)haloborates such as tetrafluoroborate, viii) carbonate, ix) bicarbonate, x) ($C_1$-$C_{12}$)alkylcarbonates, xi) dicyanamide, xii) nitrate, xiii) thiocyanate, xiv) formate, xv) ($C_1$-$C_{12}$)alkylcarboxylates in which the ($C_1$-$C_{12}$)alkyl group may be substituted with one or more halogen atoms or groups chosen from hydroxyl, ($C_1$-$C_6$)(di)(alkyl)amino, phenyl, imidazole, ($C_1$-$C_4$)alkylcarbonyl, ($C_1$-$C_4$)alkylcarbonyloxy, ($C_1$-$C_4$)alkylcarbonylamino, guanidine, thiol, —$SO_3H$, ($C_1$-$C_8$)alkoxy such as trifluoroacetate; xvi) ($C_6$-$C_{12}$)arylcarboxylates in which the aryl group may be substituted with one or more halogen atoms or groups chosen from hydroxyl, ($C_1$-$C_6$)(di)(alkyl) amino, phenyl, imidazole, ($C_1$-$C_4$)alkylcarbonyl, ($C_1$-$C_4$) alkylcarbonyloxy, ($C_1$-$C_4$)alkylcarbonylamino, guanidine, thiol, —$SO_3H$, ($C_1$-$C_8$)alkoxy; xvii) ($C_1$-$C_{12}$)alkylsulfonates in which the ($C_1$-$C_{12}$)alkyl group may be substituted with one or more halogen atoms or groups chosen from hydroxyl, ($C_1$-$C_6$)(di)(alkyl)amino, phenyl, imidazole, ($C_1$-$C_4$)alkylcarbonyl, ($C_1$-$C_4$)alkylcarbonyloxy, ($C_1$-$C_4$)alkylcarbonylamino, guanidine, thiol, —$SO_3H$, ($C_1$-$C_8$)alkoxy such as triflate, in particular ($C_1$-$C_6$)alkylsulfonates such as methylsulfonate or mesylate; and xviii) ($C_6$-$C_{12}$)arylsulfonates in which the aryl group may be substituted with one or more halogen atoms or groups chosen from hydroxyl, ($C_1$-$C_6$)(di)(alkyl)amino, phenyl, imidazole, ($C_1$-$C_4$)alkylcarbonyl, ($C_1$-$C_4$)alkylcarbonyloxy, ($C_1$-$C_4$)alkylcarbonylamino, guanidine, thiol, —$SO_3H$, ($C_1$-$C_8$)alkoxy such as benzenesulfonate and toluenesulfonate ortosylate.

Preferentially, $Y^-$ represents:

$Cl^-$ $Br^-$ $CH_3SO_3^-$ $CH_3OSO_3^-$ $CH_3OCO_2^-$ $N(CF_3SO_2)_2^-$ $N(SO_2F)_2^-$ $CF_3SO_3^-$ $PF_6^-$ $BF_4^-$ $N(CN)_2^-$ $(CH_3O)(H)PO_2^-$ $CH_3COO^-$ $HCO_3^-$ $NO_3^-$ $HCO_2^-$ $(CH_3O)_2PO_2^-$ $(CH_3CH_2O)_2PO_2^-$ $HSO_4^-$ $(nC_4H_{10}O)_2PO_2^-$ $SCN^-$ $CF_3COO^-$ $H_2PO_4^-$ $CH_3CH_2OSO_3^-$

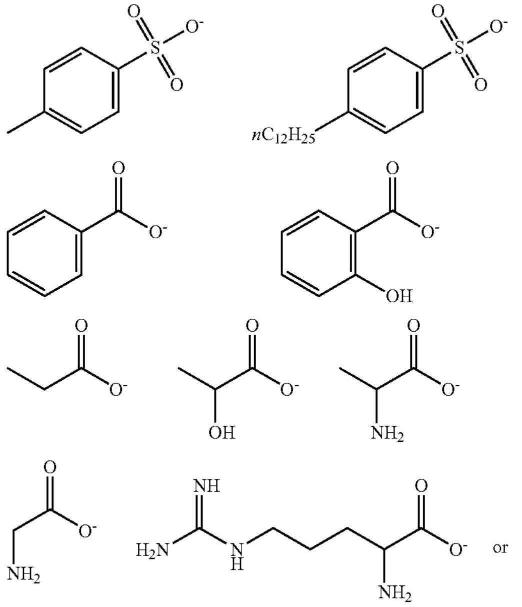

or

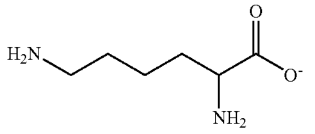

more preferentially, $Y^-$ is chosen from i), xvii) and xviii); more preferentially, $Y^-$ is chosen from chloride, bromide, methyl sulfate and tosylate.

According to a preferred embodiment of the invention, the salt(s) of formula (A), (I) or (II) are chosen from compounds 1 to 40:

1

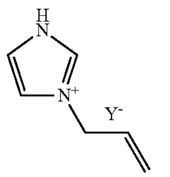

2

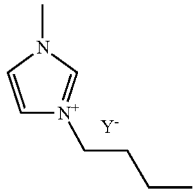

-continued
3
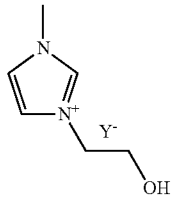
4
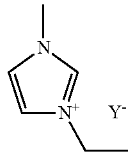
5
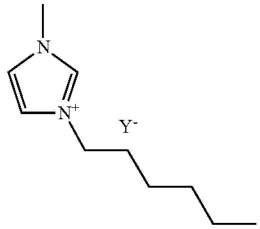
6
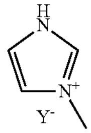
7
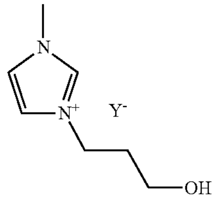
8
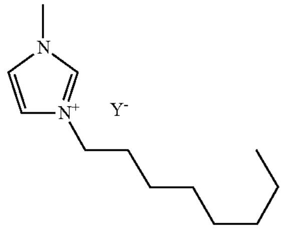
9
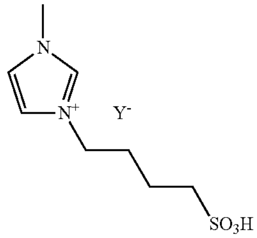
-continued
10
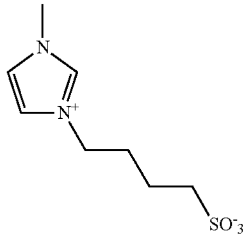
11
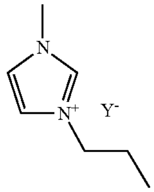
12
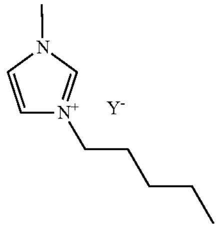
13
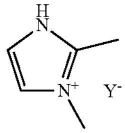
14
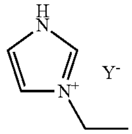
15
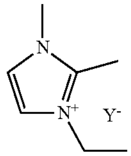
16
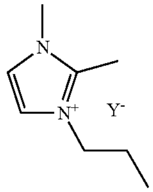
17
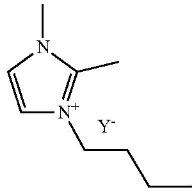

-continued
18
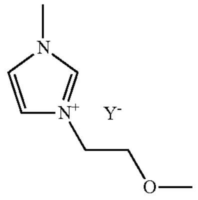
19
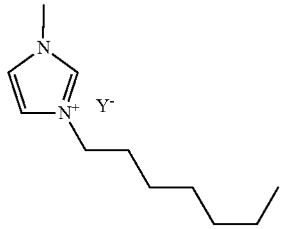
20
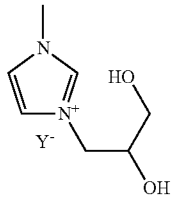
21
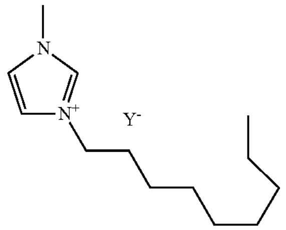
22
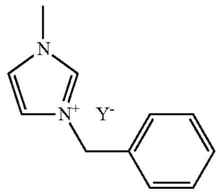
23
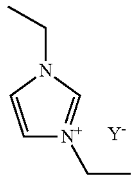
24
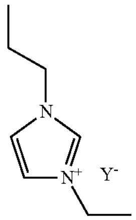
-continued
25
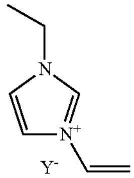
26
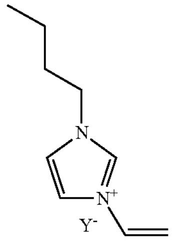
27
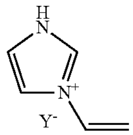
28
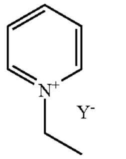
29
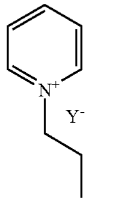
30
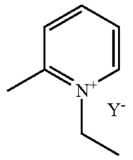
31
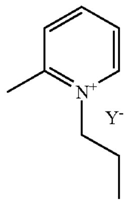
32
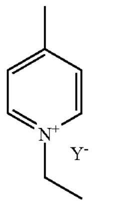

-continued

33

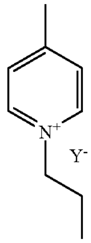

34

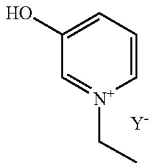

35

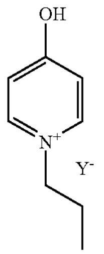

36

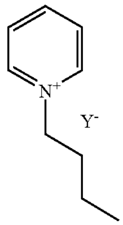

37

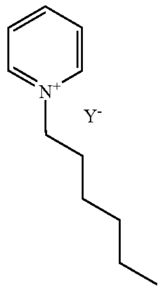

38

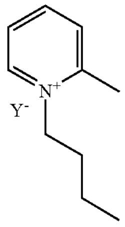

-continued

39

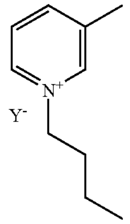

40

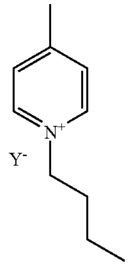

with Y' representing an anionic counterion as defined previously; preferably, the salts of formula (A), (I) or (II) are chosen from compounds 2, 3, 4, 5, 34 and 36, more preferentially 2, 4, 5 and 36.

According to a particular embodiment of the invention, the heterocyclic salt(s) of the invention are ionic liquids.

For the purposes of the present invention, the term “ionic liquid” means a salt of an organic compound, said salt having a melting point of less than or equal to 150° C., preferably less than 100° C. Preferably, the salt remains liquid up to 300° C., and more preferentially the salt is liquid at room temperature, i.e. at a temperature of less than or equal to 50° C. and greater than 0° C.

The melting point is measured by differential calorimetric analysis, with a temperature increase rate of 10° C./minute, the melting point then being at a temperature corresponding to the top of the endothermic melting peak obtained during the measurement.

The heterocyclic salt(s) (A) of the invention are preferably present in proportions ranging from 1% to 99.5% by weight, preferentially from 3% to 90%, even more preferentially from 10% to 90% by weight, better still from 20% to 80% by weight, more preferentially from 30% to 70% and even more preferentially from 40% to 60% relative to the total weight of the composition comprising them.

The Process for Dyeing Keratin Materials

The process for dyeing keratin materials, in particular keratin fibers, notably human keratin fibers such as the hair, according to the invention uses ingredients a) and b) which are applied to said fibers, together or separately, i.e. sequentially.

According to one embodiment of the invention, ingredients a) and b) are applied together to said materials. According to one variant, ingredients a) and b) are in a cosmetic composition which is applied to the keratin materials. Said cosmetic composition comprises one or more direct dyes a) as defined previously and one or more unsaturated heterocyclic salts of formula (A) as defined previously. Preferably, the cosmetic composition comprising a) and b) is aqueous. More preferentially, the composition comprises only the ingredients a), b) and water.

According to another embodiment, the process for dyeing keratin fibers of the invention comprises i) a first step of applying to the keratin materials a composition comprising a) one or more direct dyes as defined previously and then ii) a step of applying to the keratin materials a composition comprising b) one or more unsaturated heterocyclic salts of formula (A) as defined previously. Preferably, the composition comprising a) and the composition comprising b) are aqueous.

According to another particular embodiment, the process for dyeing keratin materials of the invention comprises i) a first step of applying a composition comprising b) one or more unsaturated heterocyclic salts of formula (A) as defined previously and then ii) a step of applying to the keratin materials a composition comprising a) one or more direct dyes as defined previously. Preferably, the composition comprising a) and the composition comprising b) are aqueous.

The composition(s) may be applied to wet or dry keratin materials and in particular wet or dry keratin fibers.

Preferably, the application to the keratin materials of the composition(s) comprising a) and b) as defined previously is preferably performed at room temperature, i.e. at a temperature between 25° C. and 30° C.

According to an advantageous variant of the invention, after application of ingredients a) and b), the keratin materials are rinsed, optionally shampooed and then dried or left to dry, for example at a temperature of greater than or equal to 30° C.

According to a particular embodiment, this temperature is greater than 40° C. According to a particular embodiment, this temperature is greater than 45° C. and less than 220° C.

Preferably, if the keratin materials are dried, they are dried, in addition to a supply of heat, with a flow of air.

During drying, a mechanical action may be exerted on the locks, such as combing, brushing or running the fingers through. This operation may similarly be performed once the keratin materials have been dried, naturally or otherwise.

The keratin fiber drying step of the process of the invention may be performed with a drying device such as a hood, a hairdryer, a straightening iron or a Climazon.

When the drying step is performed on keratin fibers, it may then be performed with a hood or a hairdryer; the drying temperature is between 40 and 110° C. and preferably between 50 and 90° C.

When the drying step is performed on keratin fibers, it may then be performed with a straightening iron; the drying temperature is between 110 and 220° C. and preferably between 140 and 200° C. Once the drying is complete, final rinsing or shampooing may optionally be performed.

The composition(s) applied to the wet or dry keratin materials, preferably with a weight ratio of the amount of composition applied relative to the amount of hair of between 0.1 and 10, more particularly between 0.2 and 5.

The Compositions

Another subject of the invention is a cosmetic composition which comprises a) one or more direct dyes as defined previously and b) one or more unsaturated heterocyclic salts of formula (A) as defined previously. The composition is preferably aqueous.

The composition(s) of the invention are cosmetic, i.e. they are in a cosmetic medium.

The Cosmetic Medium:

The term "cosmetic medium" means a medium that is suitable for dyeing keratin fibers, also known as a dye support, which is a cosmetic medium generally formed from water or a mixture of water and one or more organic solvents or a mixture of organic solvents. Preferably, the composition comprises water and in a content notably of between 5% and 95% inclusive relative to the total weight of the composition.

More preferentially, the composition(s) of the invention do not comprise any ingredients other than a) and b).

The term "organic solvent" means an organic substance capable of dissolving another substance without chemically modifying it.

Organic Solvents:

Examples of organic solvents that may be mentioned include lower $C_1$-$C_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

The organic solvents are preferably present in proportions preferably between inclusively 0.1% and 40% by weight approximately relative to the total weight of the dye composition, more preferentially between 1% and 30% by weight approximately and even more particularly between inclusively 5% and 25% by weight relative to the total weight of the composition.

The composition(s) of the invention may also comprise one or more compounds that are liquid at room temperature and at atmospheric pressure other than the cationic heterocyclic salts (A) of the invention. The liquid compound is preferably a solvent and in particular a solvent chosen from water, aliphatic $C_1$-$C_4$ alcohols such as ethanol and isopropanol, organic solvents which are soluble or dispersible in water such as acetone, propylene carbonate, benzyl alcohol, glycol ether derivatives, polyols such as glycerol, propylene glycol and polyethylene glycols. More preferentially, said liquid compound is a polar solvent, even more preferentially a polar protic solvent.

The pH

The pH of the composition(s) comprising ingredients a) and b) is generally between 3 and 13, preferably between 5 and 10 and more preferentially between 6 and 9.5. The pH of this or these compositions may be adjusted with acidifying or basifying agents conventionally used in cosmetics.

Among the acidifying agents, examples that may be mentioned include the organic acids already mentioned previously, or mineral acids.

The term "mineral acid" means any acid derived from a mineral compound. Among the mineral acids, mention may be made of hydrochloric acid, orthophosphoric acid, sulfuric acid, sulfonic acids and nitric acid.

Use may notably be made of mineral or organic acids such as hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines, such as monoethanolamine, diethanolamine and triethanolamine and derivatives thereof, sodium hydroxide, potassium hydroxide and the compounds of formula (B) below:

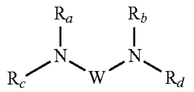

(B)

in which formula (B) W is a $(C_1$-$C_6)$alkylene group optionally substituted with one or more hydroxyl groups, $R_a$, $R_b$, $R_c$ and $R_d$, which may be identical or different, represent a hydrogen atom or a $C_1$-$C_4$ alkyl group optionally substituted with one or more hydroxyl groups. Preferably, the pH modifiers may be chosen from alkaline agents, such as aqueous ammonia, monoethanolamine, diethanolamine, triethanolamine, 1,3-propanediamine or an alkaline hydroxide, such as 2-amino-2-methyl-1-propanol, or else acidifying agents, such as phosphoric acid or hydrochloric acid.

The composition(s) comprising ingredients a) and b) may be in liquid form, in the form of a serum, in thickened form, in particular a gel, a cream, a wax or a paste, or in foam form.

The composition(s) of the invention may also comprise one or more active agents other than ingredients a) and b).

The composition used in step a) may also contain one or more additional cosmetic active agents other than solvents, reducing agents, acidic or alkaline agents and salts.

These active agents are generally chosen from nonionic, anionic, cationic or amphoteric surfactants, cationic, anionic, nonionic or zwitterionic, associative or nonassociative thickening polymers of natural or synthetic origin, silicones in the form of oils, gums or resins or non-silicone plant, mineral or synthetic oils, UV-screening agents, fillers, such as nacres and metal oxides such as titanium dioxides, clays, fragrances, peptizers, vitamins and preserving agents.

A subject of the invention is also a multi-compartment device or kit, comprising at least a first compartment which contains a) at least one direct dye as defined previously, and at least a second compartment which contains b) at least one heterocyclic salt of formula (A) as defined previously.

The invention is illustrated by the example which follows without, however, being limiting in nature.

EXAMPLES

Dyes Evaluated:

Dye 1

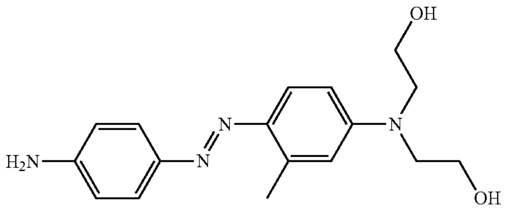

Dye 2

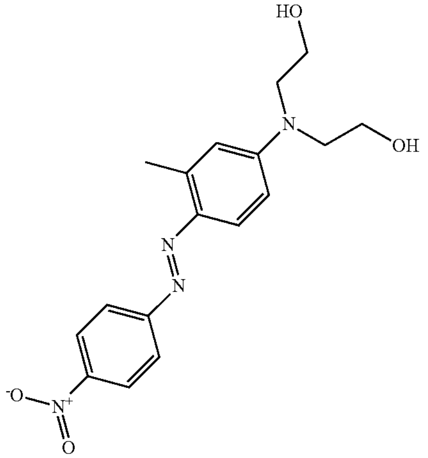

-continued

Dye 3

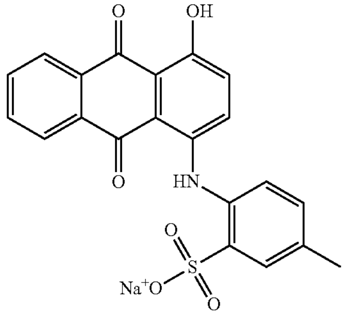

acid violet 43

Dye 4

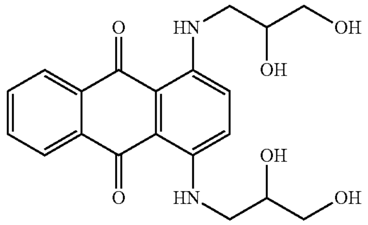

HC Blue 14

Dye 5

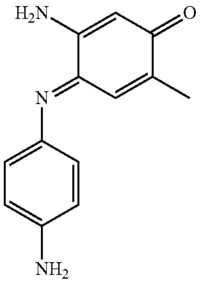

Dye 6

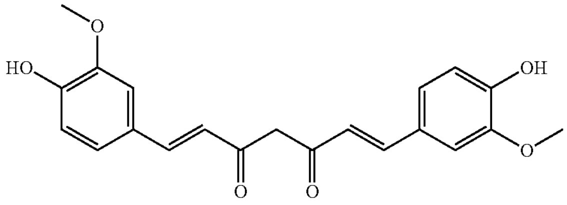

Dye 7

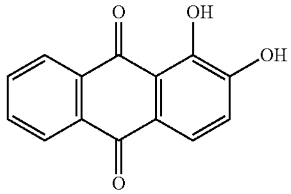

Heterocyclic Salts:

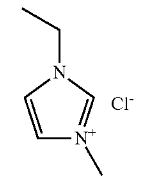

ethylmethyl imidazolium chloride

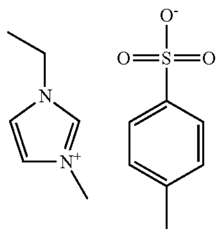

Ethylmethyl imidazolium tosylate

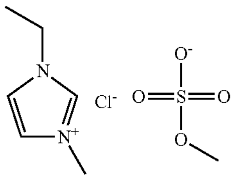

Ethylmethyl imidazolium methylsulfate

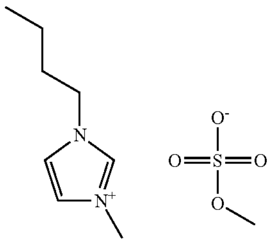

Butylmethyl imidazolium methylsulfate

-continued

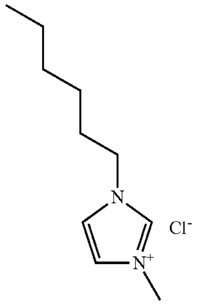

hexylmethyl imidazolium chloride

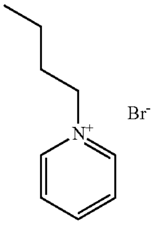

Butyl pyridinium chloride

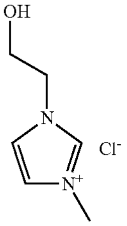

2-hydroxyethylmethyl imidazolium chloride

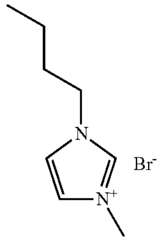

butylmethyl imidazolium bromide

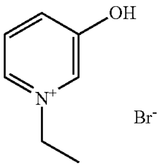

3-hydroxy-N-ethylpyridinim bromide

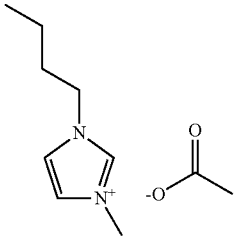

butylmethyl imidazolium acetate

Preparation of the Compositions:

The comparative compositions (Comp. 1 to 6) and the compositions of the invention (Inv. 1 to 6) were prepared by adhering to the amounts described in the tables below:

TABLE 3

| Ingredients | Comp 1 | Inv 1 | Comp. 2 | Inv. 2.1 | Inv. 2.2 | Comp. 3 | Inv. 3 |
|---|---|---|---|---|---|---|---|
| Dye 1 (g %) | 0.5 | 0.5 | — | — | — | — | — |
| Dye 2 (g %) | — | — | 0.5 | 0.5 | 0.5 | — | — |
| Dye 3 (g %) | — | — | — | — | — | 0.5 | 0.5 |
| Ethylmethylimidazolium chloride (g %) | — | 5 | — | 5 | — | — | — |
| Ethylmethylimidazolium tosylate (g %) | — | — | — | — | 5 | — | — |
| Butylpyridinium chloride (g %) | — | — | — | — | — | — | 50 |
| Water | qs 100 | qs 100 | qs 100 | qs 100 | qs 100 | qs 100 | qs 100 |

TABLE 4

| Ingredients | Comp 4 | Inv 4.1 | Inv 4.2 | Comp 5 | Inv 5.1 | Inv 5.2 | Inv 5.3 |
|---|---|---|---|---|---|---|---|
| Dye 4 (g %) | 0.5 | 0.5 | 0.5 | — | — | — | — |
| Dye 5 (g %) | — | — | — | 0.5 | 0.5 | 0.5 | 0.5 |
| Ethylmethylimidazolium tosylate (g %) | — | 50 | — | — | 50 | — | — |
| Ethylmethylimidazolium bromide (g %) | — | — | 50 | — | — | — | — |
| Ethylmethylimidazolium methyl sulfate (g %) | — | — | — | — | — | 50 | — |
| Butylmethylimidazolium methyl sulfate (g %) | — | — | — | — | — | — | 50 |
| Water | qs 100 | qs 100 | qs 100 | qs 100 | qs 100 | qs 100 | qs 100 |

TABLE 5

| Ingredients | Comp 6 | Inv 6.1 | Inv 6.2 | Inv 6.3 | Inv 6.4 |
|---|---|---|---|---|---|
| Dye 6 (g %) | 0.5 | 0.5 | 0.5 | 0.5 | 0.5 |
| Hexylmethylimidazolium chloride (g %) | — | 10 | — | — | — |
| 2-Hydroxyethylmethyl-imidazolium chloride (g %) | — | — | 10 | — | — |
| Butylmethylimidazolium bromide (g %) | — | — | — | 10 | — |
| 3-Hydroxy-N-ethylpyridinium bromide (g %) | — | — | — | — | 10 |
| Water | qs 100 | qs 100 | qs 100 | qs 100 | qs 100 |

TABLE 6

| Ingredients | Comp 7 | Inv 7.1 | Inv 7.2 | Inv 7.3 | Inv 7.4 | Inv 7.5 |
|---|---|---|---|---|---|---|
| Dye 7 (g %) | 0.5 | 0.5 | 0.5 | 0.5 | 0.5 | 0.5 |
| Hexylmethylimidazolium chloride (g %) | — | 10 | — | — | — | — |
| 2-Hydroxyethylmethylimidazolium chloride (g %) | — | — | 10 | — | — | — |
| Butylmethylimidazolium bromide (g %) | — | — | — | 10 | — | — |
| Butylmethylimidazolium acetate (g %) | — | — | — | — | 10 | — |
| 3-Hydroxy-N-ethylpyridinium bromide (g %) | — | — | — | — | — | 10 |
| Water | qs 100 | qs 100 | qs 100 | qs 100 | qs 100 | qs 100 |

TABLE 7

| Ingredients | Comp 8 | Inv 8.1 | Inv 8.2 | Inv 8.3 |
|---|---|---|---|---|
| Dye 6 (g %) | 0.5 | 0.5 | 0.5 | 0.5 |
| 2-Hydroxyethylmethylimidazolium chloride (g %) | — | 10 | — | — |
| Butylmethylimidazolium bromide (g %) | — | — | 10 | — |
| Butylmethylimidazolium acetate (g %) | — | — | — | 10 |
| Water | qs 100 | qs 100 | qs 100 | qs 100 |

Application on Locks:

Protocol 1:

5 g of Comparative composition (Comp, x) or of composition according to the invention (Inv. x) are applied to 0.5 g of natural hair containing 90% white hairs, at 33° C. for 30 minutes. The hair is then rinsed, shampooed and dried.

Protocol 2:

1 g of Comparative composition (Comp, x) or of composition according to the invention (Inv. x) is applied to 0.5 g of natural hair containing 90% white hairs, at 27° C. for 30 minutes. The hair is then rinsed, shampooed and dried.

Protocol 3:

The pH of the Comparative composition (Comp, x) or of the composition according to the invention (Inv. x) is adjusted to 3 with lactic acid and 1 g of formula is then applied to 0.5 g of natural hair containing 90% white hairs, at 27° C. for 30 minutes. The hair is then rinsed, shampooed and dried.

Protocol 4:

The pH of the Comparative composition (Comp, x) or of the composition according to the invention (Inv. x) is adjusted to 7 with aqueous ammonia and 1 g of formula is then applied to 0.5 g of natural hair containing 90% white hairs, at 27° C. for 30 minutes. The hair is then rinsed, shampooed and dried.

Protocol 5:

1 g of Comparative composition (Comp, x) or of composition according to the invention (Inv. x) is applied to 0.5 g of natural hair containing 90% white hairs, at 27° C. for 30 minutes, at a pH equal to 9.5. The hair is then rinsed, shampooed and dried.

Protocol 6:

1 g of Comparative composition (Comp, x) or of composition according to the invention (Inv. x) is applied to 0.5 g of natural hair containing 90% white hairs, at 33° C. for 30 minutes. The hair is then rinsed, shampooed and dried.

Protocol 7:

1 g of Comparative composition (Comp, x) or of composition according to the invention (Inv. x) is applied to 0.5 g of natural hair containing 90% white hairs, at 33° C. for 30 minutes, at a pH equal to 9.5. The hair is then rinsed, shampooed and dried.

Colorimetric Measurements:

The color build-up (ΔE*) was evaluated in the CIE L* a* b* system using a Minolta Spectrophotometer CM3610A colorimeter, (illuminant D65). In this L*a*b* system, L* represents the intensity of the color, a* indicates the shade of the color on the green/red color axis and b* indicates the shade of the color on the blue/yellow color axis. The lower the value of L*, the darker or more intense the color. The higher the value of a*, the redder the shade, and the higher the value of b*, the bluer the shade.

In the table below, the value of ΔE* is calculated from the values of L*a*b* according to the following equation:

$$\Delta E^* = \sqrt{(L^* - L_0^*)^2 + (a^* - a_0^*)^2 + (b^* - b_0^*)^2}$$

In the equation, L*, a* and b* represent the values measured on the locks after treatment by means of each of the protocols 1 to 4 above, and $L_0$*, $a_0$* and $b_0$* represent the values measured on untreated control locks.

The higher the ΔE* value, the better the color build-up or variation.

The results are given in the table below.

Dyeing Results:

The various build-up results obtained are given in the table below:

TABLE 6

| | Protocol | | ΔE build-up |
|---|---|---|---|
| Comparative 1 | 1 | | 21.1 |
| Invention 1 | 1 | | 31.5 |
| | Protocol | L | ΔE build-up |
| Comparative 2 | 2 | 59.3 | 8.4 |
| Invention 2.1 | 2 | 53.1 | 13.7 |
| Invention 2.2 | 2 | 53.7 | 14.0 |
| Comparative 3 | 3 | 53.0 | 15.0 |
| Invention 3 | 3 | 52.3 | 17.6 |
| Comparative 4 | 4 | 59.7 | 4.3 |
| Invention 4.1 | 4 | 55.3 | 14.6 |
| Invention 4.2 | 4 | 57.4 | 12.4 |
| Comparative 5 | 4 | 55.62 | 11.42 |
| Invention 5.1 | 4 | 45.2 | 23.5 |
| Invention 5.2 | 4 | 46.8 | 21.5 |
| Invention 5.3 | 4 | 51.1 | 15.62 |
| Comparative 6 | 6 | 59.8 | 5.6 |
| Invention 6.1 | 6 | 57.4 | 16.2 |
| Invention 6.2 | 6 | 62 | 11 |
| Invention 6.3 | 6 | 55.8 | 11.9 |
| Invention 6.4 | 6 | 61.8 | 11.6 |
| Comparative 7 | 7 | 50.2 | 16.3 |
| Invention 7.1 | 7 | 32.4 | 38 |
| Invention 7.2 | 7 | 36.8 | 32 |
| Invention 7.3 | 7 | 33.9 | 36.5 |
| Invention 7.4 | 7 | 42.5 | 23.9 |
| Invention 7.5 | 7 | 39 | 28.1 |
| Comparative 8 | 7 | 57.6 | 6.1 |
| Invention 8.1 | 7 | 59.9 | 23.7 |
| Invention 8.2 | 7 | 57.8 | 15.3 |
| Invention 8.3 | 7 | 59 | 18.1 |

It is seen from the above test results that the color build-up is significantly improved by the presence of the saturated heterocyclic salts of formula (A), irrespective of the pH tested. Moreover, the colors obtained are very vivid.

The invention claimed is:

1. A method for dyeing keratin materials, comprising applying onto the keratin materials, simultaneously or separately:

(a) at least one direct dye comprising at least one of compounds (a-A) through (a-G), salts thereof, isomers thereof, solvates thereof, or mixtures thereof:

(a-A)

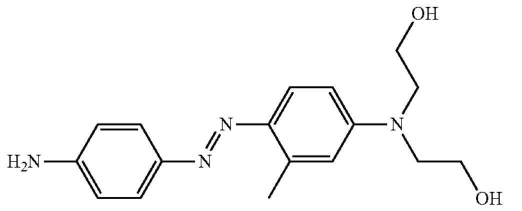

(a-B)

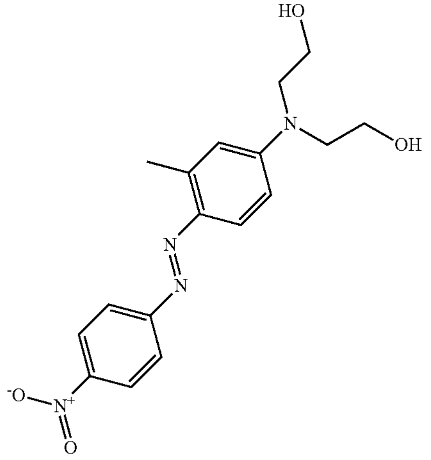

(a-C)

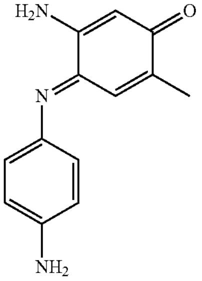

(a-D)

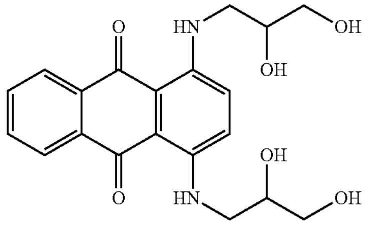

(a-E)

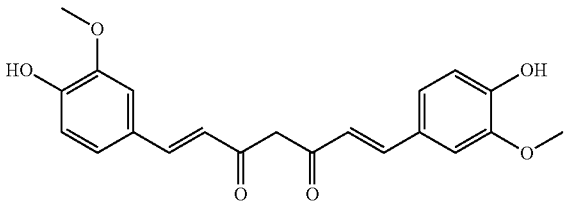

-continued
(a-F)
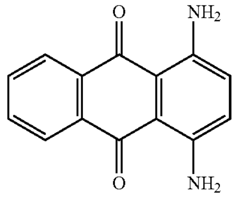
(a-G)
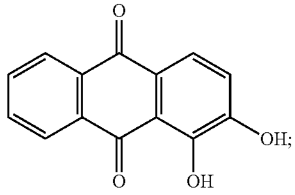
and
(b) at least one compound comprising at least one of compounds (b-1) through (b-40), optical, geometrical, or tautomeric isomers thereof, solvates thereof, or mixtures thereof:
(b-1)
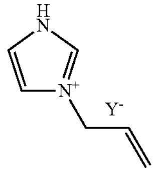
(b-2)
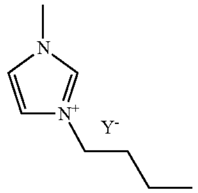
(b-3)
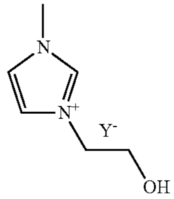
(b-4)
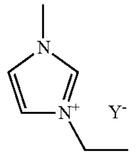
(b-5)
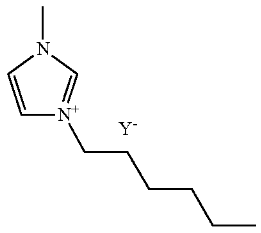
-continued
(b-6)
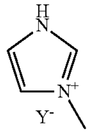
(b-7)
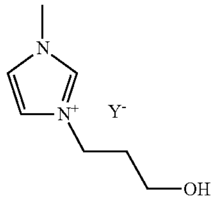
(b-8)
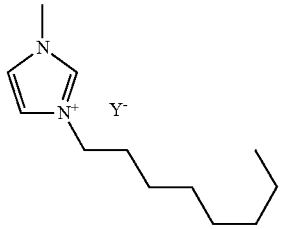
(b-9)
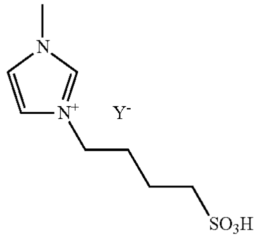
(b-10)
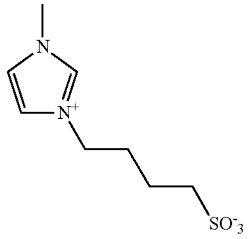
(b-11)
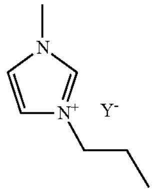
(b-12)
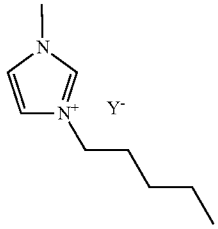

-continued
(b-13)
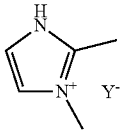
(b-14)
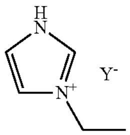
(b-15)
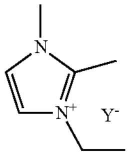
(b-16)
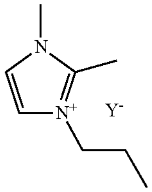
(b-17)
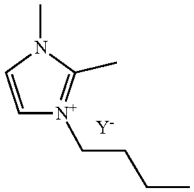
(b-18)
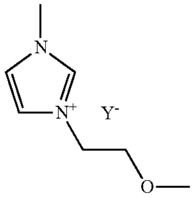
(b-19)
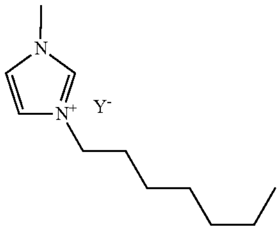
(b-20)
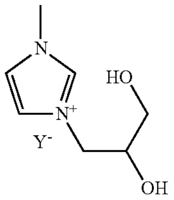
-continued
(b-21)
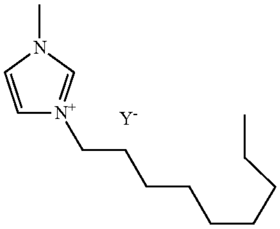
(b-22)
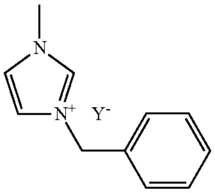
(b-23)
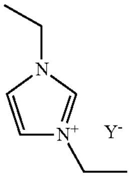
(b-24)
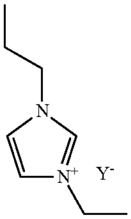
(b-25)
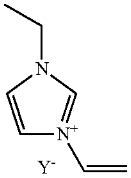
(b-26)
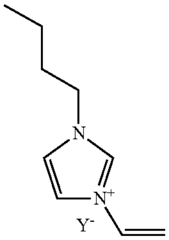
(b-27)
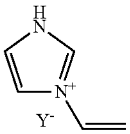
(b-28)
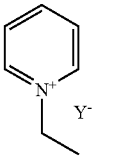

-continued (b-29)

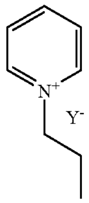

(b-30)

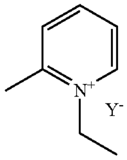

(b-31)

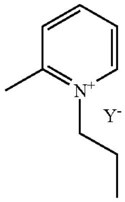

(b-32)

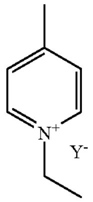

(b-33)

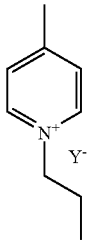

(b-34)

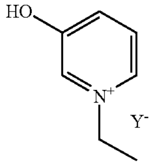

(b-35)

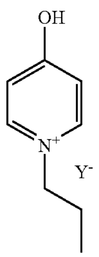

-continued (b-36)

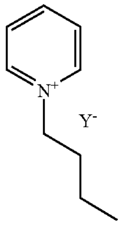

(b-37)

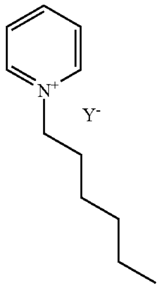

(b-38)

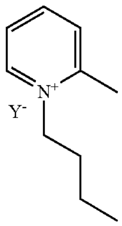

(b-39)

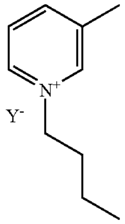

(b-40)

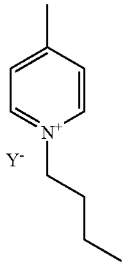

.

wherein $Y^-$ represents an anionic counterion, and wherein the at least one direct dye (a) and the at least one compound (b) are applied to the keratin materials in a total amount per gram of keratin materials effective to enhance color build-up.

2. The method according to claim 1, comprising applying onto the keratin materials a composition comprising the at least one direct dye (a) and the at least one compound (b), wherein the composition has a pH ranging from 3 and 13.

3. The method according to claim 1, comprising:

i. applying onto the keratin materials a first composition comprising the at least one direct dye (a), and subsequently applying onto the keratin materials a second composition comprising the at least one compound (b); or ii. applying onto the keratin materials a second composition comprising the at least one compound (b), and subsequently applying onto the keratin materials a first composition comprising the at least one direct dye (a);

wherein the first composition and second composition independently have a pH ranging from 3 to 13.

4. The method according to claim 1, comprising applying onto the keratin materials a composition comprising the at least one direct dye (a), wherein the total amount of direct dyes ranges from 0.001% to 10% by weight, relative to the total weight of the composition.

5. The method according to claim 1, comprising applying onto the keratin materials a composition comprising the at least one compound (b), wherein the total amount of compound (b) ranges from 1% to 99.5% by weight, relative to the total weight of the composition.

6. The method according to claim 1, comprising applying onto the keratin materials a composition comprising the at least one direct dye (a), wherein the total amount of direct dyes ranges from about 0.3% to about 3% by weight, relative to the total weight of the composition.

7. The method according to claim 1, wherein the total amount of direct dyes is about 0.5% by weight, relative to the total weight of the composition.

8. The method according to claim 1, further comprising applying onto the keratin materials at least one additional direct dye other than compounds (a-A) through (a-G).

9. The method according to claim 1, comprising applying onto the keratin materials a composition comprising the at least one compound (b), wherein the total amount of compound (b) ranges from about 3% to about 70% by weight, relative to the total weight of the composition.

10. The method according to claim 1, wherein the total amount of compound (b) ranges from about 5% to about 50% by weight, relative to the total weight of the composition.

11. The method according to claim 1, further comprising applying onto the keratin materials at least one additional compound other than compounds (b-1) through (b-40), wherein the at least one additional compound is chosen from salts of formula (A), optical, geometrical, or tautomeric isomers thereof, solvates thereof, and mixtures thereof:

(A)

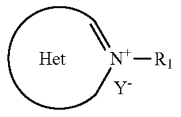

wherein in formula (A):

Het represents a 5- to 10-membered cationic unsaturated aromatic heterocyclic group comprising, besides the ammonium, from 1 to 3 heteroatoms, said heterocyclic group optionally substituted with one or more groups $R'_1$ or $R_2$;

$R_1$ and $R'_1$, which may be identical or different, represent a linear or branched, saturated or unsaturated ($C_1$-$C_{12}$) hydrocarbon-based group optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxy, —$SO_3H$, sulfonate, and phenyl;

$R_2$ represents a hydroxyl radical, an amino radical, a linear or branched, saturated or unsaturated ($C_1$-$C_{12}$) hydrocarbon-based group optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxy, —$SO_3H$, sulfonate, and phenyl; and $Y^-$ represents an anionic counterion;

with the proviso that when one of $R_1$, $R'_1$, or $R_2$ is substituted with a carboxylate or sulfonate group, $Y^-$ is absent to ensure the electrical neutrality of the salt of formula (A).

12. The method according to claim 1, wherein the at least one direct dye (a) and the at least one compound (b) are present in the same composition which is applied to the keratin fibers.

13. The method according to claim 12, wherein the composition further comprises water and optionally at least one organic solvent.

14. The method according to claim 13, wherein the composition has a pH ranging from about 6 to about 9.5.

15. The method according to claim 1, wherein the at least one direct dye (a) and the at least one compound (b) are present in different compositions which are separately applied to the keratin fibers sequentially or simultaneously.

16. The method according to claim 15, comprising applying to the keratin fibers, in order:

i) a first composition comprising the at least one direct dye (a); and ii) a second composition comprising the at least one compound (b).

17. The method according to claim 15, comprising applying to the keratin fibers, in order:

i) a first composition comprising the at least one compound (b); and ii) a second composition comprising the at least one direct dye (a).

18. The method according to claim 15, wherein the composition comprising the at least one direct dye (a) and the composition comprising the at least one compound (b) further comprise water and optionally at least one additional component chosen from organic solvents; nonionic, anionic, cationic or amphoteric surfactants; UV-screening agents; fillers; vitamins; preserving agents, or combinations thereof.

19. The method according to claim 12, wherein the composition consists essentially of the at least one direct dye (a), the at least one compound (b), and optionally water.

20. The method according to claim 1, wherein the at least one direct dye (a) and the at least one compound (b) are applied to the keratin materials at room temperature, the keratin materials are subsequently rinsed, and then the keratin materials are dried at a temperature greater than or equal to 30° C.

* * * * *